(12) United States Patent
Stossel et al.

(10) Patent No.: US 9,316,639 B2
(45) Date of Patent: Apr. 19, 2016

(54) USE OF GELSOLIN TO DIAGNOSE AND TREAT INFLAMMATORY DISEASES

(75) Inventors: Thomas P. Stossel, Belmont, MA (US); Teresia Anna Charlotta Magnuson Osborn, Belmont, MA (US); Andrej Tarkowski, Gothenburg (SE); Eric Leuchovius, legal representative, Gothenburg (SE)

(73) Assignee: The Brigham and Women's Hospital, Inc., Boston, MA (US)

( * ) Notice: Subject to any disclaimer, the term of this patent is extended or adjusted under 35 U.S.C. 154(b) by 562 days.

(21) Appl. No.: 13/455,878

(22) Filed: Apr. 25, 2012
(Under 37 CFR 1.47)

(65) Prior Publication Data

US 2012/0208743 A1  Aug. 16, 2012

Related U.S. Application Data

(63) Continuation of application No. 12/225,128, filed as application No. PCT/US2007/006451 on Mar. 15, 2007, now Pat. No. 8,198,094.

(60) Provisional application No. 60/782,508, filed on Mar. 15, 2006.

(51) Int. Cl.
*G01N 33/564* (2006.01)
*G01N 33/68* (2006.01)

(52) U.S. Cl.
CPC .......... *G01N 33/564* (2013.01); *G01N 33/6887* (2013.01); *G01N 2333/4712* (2013.01); *G01N 2800/102* (2013.01); *G01N 2800/104* (2013.01); *G01N 2800/24* (2013.01); *G01N 2800/50* (2013.01)

(58) Field of Classification Search
CPC .............. G01N 33/53; G01N 33/6887; G01N 2800/046; G01N 2800/10; G01N 2800/102; G01N 2800/104; G01N 2800/122; G01N 2800/14; G01N 2800/16; G01N 2800/24; G01N 2800/328; G01N 2800/50; G01N 2800/52; G01N 2333/4712
See application file for complete search history.

(56) References Cited

U.S. PATENT DOCUMENTS

| | | |
|---|---|---|
| 5,071,773 A | 12/1991 | Evans et al. |
| 5,260,224 A | 11/1993 | Stossel et al. |
| 5,407,821 A | 4/1995 | Breakefield et al. |
| 5,464,817 A | 11/1995 | Stossel et al. |
| 5,508,265 A | 4/1996 | Stossel et al. |
| 5,569,588 A | 10/1996 | Ashby et al. |
| 5,571,511 A | 11/1996 | Fischer |
| 5,580,265 A | 12/1996 | Koblitz et al. |
| 5,593,964 A | 1/1997 | Goldstein et al. |
| 5,656,589 A | 8/1997 | Stossel et al. |
| 5,691,160 A | 11/1997 | Janmey et al. |
| 5,744,303 A | 4/1998 | Iggo et al. |
| 5,750,353 A | 5/1998 | Kopin et al. |
| 5,783,662 A | 7/1998 | Janmey et al. |
| 5,804,427 A | 9/1998 | Davis et al. |
| 5,830,436 A | 11/1998 | Ghio et al. |
| 5,846,743 A | 12/1998 | Janmey et al. |
| 5,925,529 A | 7/1999 | Coughlin et al. |
| 6,040,147 A | 3/2000 | Ridker et al. |
| 6,271,353 B1 | 8/2001 | Nakamura et al. |
| 7,432,308 B2 | 10/2008 | Demeester et al. |
| 7,928,089 B2 | 4/2011 | Morton et al. |
| 8,198,094 B2 | 6/2012 | Stossel et al. |
| 8,440,622 B2 | 5/2013 | Stossel et al. |
| 2002/0103112 A1 | 8/2002 | Ferguson et al. |
| 2003/0083262 A1 | 5/2003 | Hannig et al. |
| 2004/0072261 A1 | 4/2004 | Kostanjevecki et al. |
| 2004/0141961 A1 | 7/2004 | Demeester et al. |
| 2006/0009386 A1* | 1/2006 | Stossel et al. .................. 514/12 |
| 2007/0087969 A1 | 4/2007 | Ferguson et al. |
| 2007/0238655 A1* | 10/2007 | Bucki et al. .................... 514/12 |
| 2007/0238668 A1 | 10/2007 | Janmey et al. |
| 2008/0125370 A1 | 5/2008 | Stossel et al. |
| 2008/0261260 A1 | 10/2008 | Stossel et al. |
| 2009/0258830 A1 | 10/2009 | Thadhani et al. |
| 2013/0230455 A1 | 9/2013 | Stossel et al. |

FOREIGN PATENT DOCUMENTS

| | | |
|---|---|---|
| CA | 2 142 121 A1 | 3/1994 |
| JP | H05-506034 A | 9/1993 |
| JP | H08-500488 A | 1/1996 |
| JP | 2004-532386 | 10/2004 |
| JP | 2005-041881 A | 2/2005 |
| JP | 2005-525998 A | 9/2005 |
| JP | 2007-524101 A | 8/2007 |
| JP | 2007-537292 A | 12/2007 |
| WO | WO 91/15770 A1 | 10/1991 |
| WO | WO 91/17170 A1 | 11/1991 |

(Continued)

OTHER PUBLICATIONS

Rothenbach PA, et al. Journal of Applied Physiology. 96:25-31, 2004 (first published May 2, 2003). Available online at—DOI: 10.1152/japplphysiol.01074.2002.*
Candiano G, et al. Am. J. Respir. Crit. Care Med. 172:1090-1096, 2005 (first published Aug. 11, 2005). Available online at—DOI: 10.1164/rccm.200409-1185OC.*
Christofidou-Solomidou M, et al. J. Invest. Med. 50(1):54-60, Jan. 2002.*
Rooney M., et al. Rheumatol. Int. 10:217-219, 1990.*
Kucan Jo, et al., J. Surgical Research, 24(2):79-82, Feb. 1978—available online at DOI: http://dx.doi.org/10.1016/0022-4804(78)90077-X.*

(Continued)

*Primary Examiner* — Robert Landsman
(74) *Attorney, Agent, or Firm* — Wolf, Greenfield & Sacks, P.C.

(57) ABSTRACT

The invention relates to the use of gelsolin to treat inflammatory diseases (e.g., rheumatoid arthritis) and to the use of gelsolin to diagnose, monitor, and evaluate therapies of inflammatory diseases (e.g., rheumatoid arthritis).

18 Claims, 2 Drawing Sheets

(56) References Cited

FOREIGN PATENT DOCUMENTS

| | | |
|---|---|---|
| WO | WO 94/04704 A1 | 3/1994 |
| WO | WO 94/22465 A1 | 10/1994 |
| WO | WO 95/09645 A1 | 4/1995 |
| WO | WO 00/55350 A1 | 9/2000 |
| WO | WO 02/059604 A2 | 8/2002 |
| WO | WO 03/020213 A2 | 3/2003 |
| WO | WO 03/088811 A2 | 10/2003 |
| WO | WO 2004/023973 A2 | 3/2004 |
| WO | WO 2004/035008 A2 | 4/2004 |
| WO | WO 2004/082617 A2 | 9/2004 |
| WO | WO 2005/046454 A2 | 5/2005 |
| WO | WO 2005/085859 A1 | 9/2005 |
| WO | WO 2005/112970 A2 | 12/2005 |
| WO | WO 2007/041245 A2 | 4/2007 |
| WO | WO 2007/106577 A2 | 9/2007 |
| WO | WO 2007/109056 A2 | 9/2007 |
| WO | WO 2009/094194 A2 | 7/2009 |

OTHER PUBLICATIONS

Genbank Submission; NIH/NCBI, Accession No. 1211330A; Kwiatkowski et al.; Oct. 1, 1996. Last accessed Feb. 3, 2005 at http:ncbi.nlm.nih.gov/entrez/viewer.fcgi?db=protein&val=225304. 2 pages.

Genbank Submission; NIH/NCBI, Accession No. CAA28000; Kwiatkowski et al.; Mar. 21, 1995. Last accessed Feb. 3, 2005 at http:ncbi.nlm.nih.gov/entrez/viewer.fcgi?db=protein&val=736249. 2 pages.

Genbank Submission; NIH/NCBI, Accession No. X04412.1; Kwiatkowski et al.; Oct. 7, 2008.

[No Author Listed] "Risk". Dorlands Medical Dictionary. Merck Source. Last accessed on Jun. 29, 2009 available at www.mercksource.com/pp/us/cns/snc_hl_dorlands_split.jsp?pg=/ppdocs/us/common/dorlands/dorland/seven/000093452.html, 2009.2 pages.

[No Author Listed] "Risk". Medical Dictionary. Last accessed on Jun. 29, 2009 available at www.medicaldictionaryweb.com/Rish-definition/2009. 1 page.

[No Author Listed] "Risk". Rogets II The New Thesaurus NY, Expanded Edition. Houghton Mifflin Company. New York 1988:843.

[No Author Listed] Choice of Control Group and Related Issues in Clinical Trials, E10. ICH Harmonised Tripartite Guideline. International Conference on Harmonisation of Technical Requirements for Registration of Pharmaceuticals for Human Use. Jul. 20, 2000. 35 pages.

[No Author Listed] E10 Choice of Control Group and Related Issues in Clinical Trials. Guidance for Industry. U.S. Department of Health and Human Services, Food and Drug Administration, Center for Drug Evaluation and Research (CDER), and Center for Biologics Evaluation and Research (CBER). May 2001. 37 pages.

[No Author Listed] Pharmacokinetics in Patients with Impaired Hepatic Function: Study Design, Data Analysis, and Impact on Dosing and Labeling. Guidance for Industry. U.S. Department of Health and Human Services, Food and Drug Administration, Center for Drug Evaluation and Research (CDER), and Center for Biologics Evaluation and Research (CBER). May 2003. 19 pages.

Adams et al., Fibrin mechanisms and functions in nervous system pathology. Mol Interv. Jun. 2004;4(3):163-76.

Aidinis et al., Cytoskeletal rearrangements in synovial fibroblasts as a novel pathophysiological determinant of modeled rheumatoid arthritis. PLoS Genet. Oct. 2005;1(4):e48. Epub Oct. 28, 2005. 12 pages.

Angus et al., Epidemiology of sepsis: an update. Crit Care Med. Jul. 2001;29(7 Suppl):S109-16.

Badid et al., Role of myofibroblasts during normal tissue repair and excessive scarring: interest of their assessment in nephropathies. Histol Histopathol. Jan. 2000;15(1):269-80.

Bannerman et al., Increased levels of LPS-binding protein in bovine blood and milk following bacterial lipopolysaccharide challenge. J Dairy Sci. Oct. 2003;86(10):3128-37.

Barnard et al., Targeted deletion of gelsolin potentiates endotoxin-induced murine lung vascular leak. FASEB. 2004;18(4-5):A352. Abstract 233.8.

Becker et al., Pulmonary vascular permeability and ischemic injury in gelsolin-deficient mice. Am J Respir Cell Mol Biol. Apr. 2003;28(4):478-84.

Beddhu et al., Inflammation and inverse associations of body mass index and serum creatinine with mortality in hemodialysis patients. J Ren Nutr. Nov. 2007;17(6):372-80.

Berer et al., Are the serum levels of endotoxin-binding proteins reliable predictors of complications in the course of peritonitis? Eur J Clin Invest. Feb. 1990;20(1):66-71.

Berger et al, Evidence for endotoxin binding capacity of human Gc-globulin and transferrin. Clin Chim Acta. Mar. 30, 1987;163(3):289-99.

Beutler et al, Sepsis and evolution of the innate immune response. Crit Care Med. Jul. 2001;29(7 Suppl):S2-6; discussion S6-7.

Bochicchio et al., Reclassification of urinary tract infections in critically ill trauma patients: a time-dependent analysis. Surg Infect (Larchmt). 2003 Winter;4(4):379-85. Abstract only.

Bosshart et al., Endotoxin-neutralizing effects of histidine-rich peptides. FEBS Lett. Oct. 9, 2003;553(1-2):135-40.

Bowman et al., Cultured astrocytes express toll-like receptors for bacterial products. Glia. Sep. 2003;43(3):281-91.

Brandenburg et al., Physicochemical properties of bacterial glycopolymers in relation to bioactivity. Carbohydr Res. Nov. 14, 2003;338(23):2477-89.

Brettschneider et al., Tau protein level in cerebrospinal fluid is increased in patients with early multiple sclerosis. Mult Scler. Jun. 2005;11(3):261-5.

Bsibsi et al., Broad expression of Toll-like receptors in the human central nervous system. J Neuropathol Exp Neurol. Nov. 2006;61(11):1013-21.

Bucki et al., Antibacterial activities of rhodamine B-conjugated gelsolin-derived peptides compared to those of the antimicrobial peptides cathelicidin LL37, magainin II, and melittin. Antimicrob Agents Chemother. May 2004;48(5):1526-33.

Bucki et al., Bacterial endotoxin as inhibitor of the enzymatic activity of human thrombin. Eur J Haematol. Jun. 2006;76(6):510-5. Epub Mar. 9, 2006.

Bucki et al., Extracellular gelsolin binds lipoteichoic acid and modulates cellular response to proinflammatory bacterial wall components. J Immunol. Oct. 1, 2008;181(7):4936-44.

Bucki et al., Inactivation of endotoxin by human plasma gelsolin. Biochemistry. Jul. 19, 2005;44(28):9590-7.

Bucki et al., Plasma gelsolin: function, prognostic value, and potential therapeutic use. Curr Protein Pept Sci. Dec. 2008;9(6):541-51.

Candiano et al., Gelsolin secretion in interleukin-4-treated bronchial epithelia and in asthmatic airways. Am J Respir Crit Care Med. Nov. 1, 2005;172(9):1090-6. Epub Aug. 11, 2005.

Casas et al., Reconstituted high-density lipoprotein reduces LPS-stimulated TNF alpha. J Surg Res. Nov. 1995;59(5):544-52.

Chauhan et al., Binding of gelsolin, a secretory protein, to amyloid beta-protein. Biochem Biophys Res Commun. May 10, 1999;258(2):241-6.

Chavko et al., Lung injury and recovery after exposure to blast overpressure. J Trauma. Oct. 2006;61(4):933-42.

Chebotareva et al., [The role of smooth muscle alpha-actin in development of renal fibrosis in patients with chronic glomerulonephritis]. Ter Arkh. 2006;78(5):17-21.

Chen, Multiple Sclerosis. Chinese Medicine Press. Jun. 30, 2000;67-73.

Christofidou-Solomidou et al., Changes in plasma gelsolin concentration during acute oxidant lung injury in mice. Lung. 2002;180(2):91-104.

Christofidou-Solomidou et al., Recombinant plasma gelsolin diminishes the acute inflammatory response to hyperoxia in mice. J Investig Med. Jan. 2002;50(1):54-60.

Cirioni et al., Potential therapeutic role of histatin derivative P-113d in experimental rat models of Pseudomonas aeruginosa sepsis. J Infect Dis. Jul. 15, 2004;190(2):356-64. Epub Jun. 21, 2004.

(56) References Cited

OTHER PUBLICATIONS

Cohen et al., Therapeutic potential of plasma gelsolin administration in a rat model of sepsis. Cytokine. Jun. 2011;54(3):235-8. Epub Mar. 21, 2011.
Cunningham et al., Cell permeant polyphosphoinositide-binding peptides that block cell motility and actin assembly. J Biol Chem. Nov. 16, 2011;276(46):43390-9. Epub Aug. 30, 2001.
Dahl et al., Plasma concentration of Gc-globulin is associated with organ dysfunction and sepsis after injury. Crit Care Med. Jan. 2003;31(1):152-6.
Dahl et al., Plasma gelsolin is reduced in trauma patients. Shock. Aug. 1999;12(2):102-4.
Dahl et al., Serum Gc-globulin in the early course of multiple trauma. Crit Care Med. Feb. 1998;26(2):285-9.
Dinubile et al., Decreased gelsolin levels are associated with interstitial pneumonia after allogenic BMT. Blood. 1998;92(Suppl):683a. Abstract 2814.
Dinubile et al., Prognostic implications of declining plasma gelsolin levels after allogeneic stem cell transplantation. Blood. Dec. 15, 2002;100(13):4367-71. Epub Aug. 1, 2002.
Dou, Immunocytology and Disease. Chapter 11. Chinese Medical Science and Technology Press. Sep. 30, 2004;404-415, Y—Abstract Only.
Erridge et al., Structure and function of lipopolysaccharides. Microbes Infect. Jul. 2002;4(8):837-51.
Erukhimov et al., Actin-containing sera from patients with adult respiratory distress syndrome are toxic to sheep pulmonary endothelial cells. Am J Respir Crit Care Med. Jul. 2000;162(1):288-94.
Faure et al., Bacterial lipopolysaccharide activates NF-kappaB through toll-like receptor 4 (TLR-4) in cultured human dermal endothelial cells. Differential expression of TLR-4 and TLR-2 in endothelial cells. J Biol Chem. Apr. 14, 2000;275(15):11058-63.
Flanagan et al., The structure of divalent cation-induced aggregates of PIP2 and their alteration by gelsolin and tau. Biophys J. Sep. 1997;73(3):1440-7.
Fouque et al., A proposed nomenclature and diagnostic criteria for protein-energy wasting in acute and chronic kidney disease. Kidney Int. Feb. 2008;73(4):391-8. Epub Dec. 19, 2007.
Ginsburg, Role of lipoteichoic acid in infection and inflammation. Lancet Infect Dis. Mar. 2002;2(3):171-9.
Goetzl et al., Gelsolin binding and cellular presentation of lysophosphatidic acid. J Biol Chem. May 12, 2000;275(19):14573-8.
Goetzl, Pleiotypic mechanisms of cellular responses to biologically active lysophospholipids. Prostaglandins. Apr. 2001;64(1-4):11-20.
Goldschmidt-Clermont et al., Role of group-specific component (vitamin D binding protein) in clearance of actin from the circulation in the rabbit. J Clin Invest. May 1988; 81(5):1519-27.
Grant et al., Reversal of Paralysis and Reduced Inflammation from Peripheral Administration of Amyloid-β in Th1- and Th17-Versions of Experimental Autoimmune Encephalomyelitis. Sci Transl Med. Aug 1, 2012; 4(145): 145ra105.
Güntert et al., Plasma gelsolin is decreased and correlates with rate of decline in Alzheimer's disease. J Alzheimers Dis. 2010;21(2):585-96. Abstract only.
Gutsmann et al., Dual role of lipopolysaccharide (LPS)-binding protein in neutralization of LPS and enhancement of LPS-induced activation of mononuclear cells. Infect Immun. Nov. 2001;69(11):6942-50.
Haddad et al., Angiopathic consequences of saturating the plasma scavenger system for actin. Proc Natl Acad Sci U S A. Feb. 1990;87(4):1381-5.
Harris et al., Lipoprotein-bound LPS induces cytokine tolerance in hepatocytes. J Endotoxin Res. 2003;9(1):45-50.
Hartung et al., Inflammatory mediators in demyelinating disorders of the CNS and PNS. J Neuroimmunol. Oct. 1992;40(2-3):197-210.
Hattar et al., Lipoteichoic acid (LTA) from *Staphylococcus aureus* stimulates human neutrophil cytokine release by a CD14-dependent, Toll-like-receptor-independent mechanism: Autocrine role of tumor necrosis factor-[alpha] in mediating LTA-induced interleukin-8 generation. Crit Care Med. Mar. 2006;34(3):835-41.
Hayter et al., Neutron scattering analysis of bacterial lipopolysaccharide phase structure. Changes at high pH. J Biol Chem. Apr. 15, 1987;262(11):5100-5.
Himmelfarb et al., The elephant in uremia: oxidant stress as a unifying concept of cardiovascular disease in uremia. Kidney Int. Nov. 2002;62(5):1524-38.
Hsueh et al., Hypertension, the endothelial cell, and the vascular complications of diabetes mellitus. Hypertension. Aug. 1992;20(2):253-63.
Huang et al, Temporal association between serum gelsolin levels and clinical events in a patient with severe falciparum malaria. Clin Infect Dis. May 1997;24(5):951-4.
Hummell et al., Bacterial lipoteichoic acid sensitizes host cells for destruction by autologous complement. J Clin Invest. May 1986;77(5):1533-8.
Hyde et al., Mortality and bacteriology of sepsis following cecal ligation and puncture in aged mice. Infect Immun. Mar. 1990;58(3):619-24.
Igarashi et al., Sphingosine-phosphate content in the plasma of platelet concentrates correlates with poor platelet increments after transfusion and with occurrences of transfusion reactions in patients. Am J Hematol. Mar. 1998;57(3):261-2.
Ito et al., Depression of plasma gelsolin level during acute liver injury. Gastroenterology. May 1992;102(5):1686-92.
Janmey et al., Capacity of human serum to depolymerize actin filaments. Blood. Aug. 1987;70(2):524-30.
Janmey et al., Deconstructing gelsolin: identifying sites that mimic or alter binding to actin and phosphoinositides. Chem Biol. Apr. 1998;5(4):R81-5.
Janmey et al., Functional comparison of villin and gelsolin. Effects of Ca2+, KCl, and polyphosphoinositides. J Biol Chem. Nov. 15, 1988;263(32):16738-43.
Janmey et al., Interactions of gelsolin and gelsolin-actin complexes with actin. Effects of calcium on actin nucleation, filament severing, and end blocking. Biochemistry. Jul. 2, 1985;24(14):3714-23.
Janmey et al., Modulation of gelsolin function by phosphatidylinositol 4,5-bisphosphate. Nature. Jan. 22-28, 1987;325(6102):362-4.
Janmey et al., Polyphosphoinositide micelles and polyphosphoinositide-containing vesicles dissociate endogenous gelsolin-actin complexes and promote actin assembly from the fast-growing end of actin filaments blocked by gelsolin. J Biol Chem. Sep. 5, 1987;262(25):12228-36.
Janmey, Phosphoinositide-binding peptides derived from the sequences of gelsolin and villin. J Biol Chem. Jun. 15, 1992;267(17):11818-23.
Jensen et al., Features of endothelial dysfunction in early diabetic nephropathy. Lancet. Mar. 4, 1989;1(8636):461-3.
Ji et al., Gelsolin levels are increased in the brain as a function of age during normal development in children that are further increased in Down syndrome. Alzheimer Dis Assoc Disord. Oct.-Dec. 2009;23(4):319-22.
Jordan et al., Gelsolin is depleted in post-shock mesenteric lymph. J Surg Res. Nov. 2007;143(1):130-5. doi: 10.1016/j.jss.2007.04.017.
Jorgensen et al., Peptidoglycan and lipoteichoic acid modify monocyte phenotype in human whole blood. Clin Diagn Lab Immunol. May 2001;8(3):515-21.
Kalantar-Zadeh et al., A malnutrition-inflammation score is correlated with morbidity and mortality in maintenance hemodialysis patients. Am J Kidney Dis. Dec. 2001;38(6):1251-63.
Kalantar-Zadeh et al., Effect of malnutrition-inflammation complex syndrome on EPO hyporesponsiveness in maintenance hemodialysis patients. Am J Kidney Dis. Oct. 2003;42(4):761-73.
Kawamura et al., Lipoteichoic acid-induced neutrophil adhesion via E-selectin to human umbilical vein endothelial cells (HUVECs). Biochem Biophys Res Commun. Dec. 26, 1995;217(3):1208-15.
Kaysen et al., Longitudinal and cross-sectional effects of C-reactive protein, equilibrated normalized protein catabolic rate, and serum bicarbonate on creatinine and albumin levels in dialysis patients. Am J Kidney Dis. Dec. 2003;42(6):1200-11.

(56) References Cited

OTHER PUBLICATIONS

Kent et al., A monoclonal antibody to alpha 4 integrin suppresses and reverses active experimental allergic encephalomyelitis. J Neuroimmunol. Apr. 1995;58(1):1-10.
Kouyama et al., Fluorimetry study of N-(1-pyrenyl)iodoacetamide-labelled F-actin. Local structural change of actin protomer both on polymerization and on binding of heavy meromyosin. Eur J Biochem. 1981;114(1):33-8.
Kułakowska et al., Depletion of plasma gelsolin in patients with tick-borne encephalitis and Lyme neuroborreliosis. Neurodegener Dis. 2011;8(5):375-80.
Kułakowska et al., Gelsolin concentration in cerebrospinal fluid from patients with multiple sclerosis and other neurological disorders. Eur J Neurol. Jun. 2008;15(6):584-8.
Kułakowska et al., Hypogelsolinemia, a disorder of the extracellular actin scavenger system, in patients with multiple sclerosis. BMC Neurol. Nov. 1, 2010;10:107. 8 pages.
Kwiatkowski, Functions of gelsolin: motility, signaling, apoptosis, cancer. Curr Opin Cell Biol. Feb. 1999;11(1):103-8.
Kwiatkowski et al., Identification of critical functional and regulatory domains in gelsolin. J Cell Biol. May 1989;108(5):1717-26.
Kwiatkowski et al., Isolation and properties of two actin-binding domains in gelsolin. J Biol Chem. Dec. 5, 1985;260(28):15232-8.
Kwiatkowski et al., Muscle is the major source of plasma gelsolin. J Biol Chem. Jun. 15, 1988;263(17):8239-43.
Kwiatkowski et al., Plasma and cytoplasmic gelsolins are encoded by a single gene and contain a duplicated actin-binding domain. Nature. Oct. 2-8, 1986;323(6087):455-8.
Lazarus et al., Role of bioincompatibility in dialysis morbidity and mortality. Am J Kidney Dis. Dec. 1994;24(6):1019-32.
Lee et al., Plasma gelsolin and circulating actin correlate with hemodialysis mortality. J Am Soc Nephrol. May 2009;20(5):1140-8. Epub Apr. 23, 2009.
Lee et al., Plasma Gelsolin Depletion and Circulating Actin in Sepsis: A Pilot Study. PLoS One. 2008;3(11):e3712. doi:10.1371/journal.pone.0003712. 5 pages.
Lee et al., Plasma Gelsolin Is a Critical Pro-Survival Factor in Sepsis. American Thoracic Society. 2005. Last accessed Feb. 15, 2012 at http://www.mindcull.com/data/american-thoracic-society/ats-2005-american-thoracic-soci . . . Abstract only. 1 page.
Lee et al., Plasma gelsolin is a marker and therapeutic agent in animal sepsis. Crit Care Med. Mar. 2007;35(3):849-55.
Lee et al., Plasma Gelsolin Levels Predict the Outcomes of Critically Ill Patients in Surgical Intensive Care Unit. American Thoracic Society International Conference. Apr. 2004;167(7):A627. (ATS 2004—Orlando).
Lee et al., Relationship of plasma gelsolin levels to outcomes in critically ill surgical patients. Ann Surg. Mar. 2006;243(3):399-403.
Lee et al., The extracellular actin-scavenger system and actin toxicity. N Engl J Med. May 14, 1992;326(20):1335-41.
Lee et al., The potential role of plasma gelsolin in dialysis-related protein-energy wasting. Blood Purif. 2010;29(2):99-101. Epub Jan. 8, 2010.
Li et al., The critical micelle concentrations of lysophosphatidic acid and sphingosylphosphorylcholine. Chem Phys Lipids. Jul. 2004;130(2):197-201.
Liao et al., Overexpression of gelsolin in human cervical carcinoma and its clinicopathological significance. Gynecol Oncol. Jan. 2011;120(1):135-44.
Liepina et al., Molecular dynamics study of a gelsolin-derived peptide binding to a lipid bilayer containing phosphatidylinositol 4,5-bisphosphate. Biopolymers. 2003;71(1):49-70.
Lind et al., Depression of gelsolin levels and detection of gelsolin-actin complexes in plasma of patients with acute lung injury. Am Rev Respir Dis. Aug. 1988;138(2):429-34.
Lind et al., Human plasma gelsolin binds to fibronectin. J Biol Chem. Nov. 10, 1984;259(21):13262-6.
Lind et al., Role of plasma gelsolin and the vitamin D-binding protein in clearing actin from the circulation. J Clin Invest. Sep. 1986;78(3):736-42.
Löfberg et al., Serum gelsolin and rhabdomyolysis. J Neurol Sci. May 7, 1998;157(2):187-90.
Masover et al., The effect of growth and urea concentration on ammonia production by a urea-hydrolysing mycoplasma (*Ureaplasma urealyticum*). J Gen Microbiol. Feb. 1977;98(2):587-93.
Mathison et al., Plasma lipopolysaccharide (LPS)-binding protein. A key component in macrophage recognition of gram-negative LPS. J Immunol. Jul. 1, 1992;149(1):200-6.
Matsumoto et al., Diagnosis of sepsis based on the host response. The Official Journal of Japanese Society of Laboratory Medicine. 1999;47(6):494-500. Japanese language reference.
Matsuoka et al., Novel therapeutic approach for the treatment of Alzheimer's disease by peripheral administration of agents with an affinity to beta-amyloid. J Neurosci. Jan. 1, 2003;23(1):29-33.
Matthay et al., Acute lung injury and the acute respiratory distress syndrome: four decades of inquiry into pathogenesis and rational management. Am J Respir Cell Mol Biol. Oct. 2005;33(4):319-27.
Maury, Homozygous familial amyloidosis, Finnish type: demonstration of glomerular gelsolin-derived amyloid and non-amyloid tubular gelsolin. Clin Nephrol. Jul. 1993;40(1):53-6. Abstract only.
Maury et al., Homozygosity for the Asn187 gelsolin mutation in Finnish-type familial amyloidosis is associated with severe renal disease. Genomics. Jul. 1992;13(3):902-3.
McIntyre et al., Patients receiving maintenance dialysis have more severe functionally significant skeletal muscle wasting than patients with dialysis-independent chronic kidney disease. Nephrol Dial Transplant. Aug. 2006;21(8):2210-6. Epub Feb. 27, 2006.
Meerschaert et al., Gelsolin and functionally similar actin-binding proteins are regulated by lysophosphatidic acid. EMBO J. Oct. 15, 1998;17(20):5923-32.
Mertsola et al., Release of endotoxin after antibiotic treatment of Gram-negative bacterial meningitis. Pediatr Infect Dis J. Dec. 1989;8(12):904-6.
Mezzano et al., Endothelial cell markers in chronic uremia: relationship with hemostatic defects and severity of renal failure. Thromb Res. Dec. 15, 1997;88(6):465-72.
Mezzano et al., Inflammation, not hyperhomocysteinemia, is related to oxidative stress and hemostatic and endothelial dysfunction in uremia. Kidney Int. Nov. 2001;60(5):1844-50.
Mintzer et al., Lysophosphatidic acid and lipopolysaccharide bind to the PIP2-binding domain of gelsolin. Biochim Biophys Acta. Jan. 2006;1758(1):85-9. Epub Jan. 18, 2006.
Mitch et al., Mechanisms of muscle wasting. The role of the ubiquitin-proteasome pathway. N Engl J Med. Dec. 19, 1996;335(25):1897-905.
Morgan, Risk factors for infection in the trauma patient. J Natl Med Assoc. Dec. 1992; 84(12):1019-23.
Moss, Epidemiology of sepsis: race, sex, and chronic alcohol abuse. Clin Infect Dis. Nov. 15, 2005;41 Suppl 7:S490-7.
Mounzer et al., Relationship of admission plasma gelsolin levels to clinical outcomes in patients after major trauma. Am J Respir Crit Care Med. Nov. 1999;160(5 Pt 1):1673-81.
Myers et al., Collagen-induced arthritis, an animal model of autoimmunity. Life Sci. 1997;61(19):1861-78.
Nandakumar et al., Efficient promotion of collagen antibody induced arthritis (CAIA) using four monoclonal antibodies specific for the major epitopes recognized in both collagen induced arthritis and rheumatoid arthritis. J Immunol Methods. Sep. 2005;304(1-2):126-36.
Ni et al., The ubiquitin-proteasome pathway mediates gelsolin protein downregulation in pancreatic cancer. Mol Med. Sep.-Oct. 2008;14(9-10):582-9.
Nollet et al., Protection of just weaned pigs against infection with F18+ *Escherichia coli* by non-immune plasma powder. Vet Microbiol. Feb. 23, 1999;65(1):37-45.
Nugent et al., Sphingosine-1-phosphate: characterization of its inhibition of platelet aggregation. Platelets. Jun. 2000;11(4):226-32.
Osborn et al., Decreased levels of the gelsolin plasma isoform in patients with rheumatoid arthritis. Arthritis Res Ther. 2008;10(5):R117. Epub Sep. 27, 2008. 9 pages.

(56) References Cited

OTHER PUBLICATIONS

Osborn et al., Modifications of cellular responses to lysophosphatidic acid and platelet-activating factor by plasma gelsolin. Am J Physiol Cell Physiol. Apr. 2007;292(4):C1323-30. Epub Nov. 29, 2006.
Otero-Antón et al. Cecal ligation and puncture as a model of sepsis in the rat: influence of the puncture size on mortality, bacteremia, endotoxemia and tumor necrosis factor alpha levels. Eur Surg Res. 2001;33(2):77-9.
Overhaus et al., Mechanisms of polymicrobial sepsis-induced ileus. Am J Physiol Gastrointest Liver Physiol. Sep. 2004;287(3):G685-94.
Overland et al., Lipoteichoic acid is a potent inducer of cytokine production in rat and human Kupffer cells in vitro. Surg Infect (Larchmt). 2003 Summer;4(2):181-91.
Owen et al., The urea reduction ratio and serum albumin concentration as predictors of mortality in patients undergoing hemodialysis. N Engl J Med. Sep. 30, 1993;329(14):1001-6.
Pottiez et al., Mass spectrometric characterization of gelsolin isoforms. Rapid Commun Mass Spectrom. Sep. 15, 2010;24(17):2620-4.
Riedermann et al., The enigma of sepsis. J Clin Invest. Aug. 2003;112(4):460-7.
Robinson, Amyloid beta reverses MS-like disease in mice. Is it time to reevaluate amyloid elsewhere? Sep. 2012:16-17.
Rogers et al., Relationship of Gelsolin Levels to Outcomes in Critically Ill Patients. J Surg Res. 2002;107(2):305-6.
Rothenbach et al., Recombinant plasma gelsolin infusion attenuates burn-induced pulmonary microvascular dysfunction. J Appl Physiol. Jan. 2004;96(1):25-31. Epub May 2, 2003.
Rustici et al., Molecular mapping and detoxification of the lipid a binding site by synthetic peptides. Science. Jan. 15, 1993;259(5093):361-5.
Salat et al., The relevance of plasminogen activator inhibitor 1 (PAI-1) as a marker for the diagnosis of hepatic veno-occlusive disease in patients after bone marrow transplantation. Leuk Lymphoma. Mar. 1999;33(1-2):25-32.
Saura et al., Microglial apolipoprotein E and astroglial apolipoprotein J expression in vitro: opposite effects of lipopolysaccharide. J Neurochem. Jun. 2003;85(6):1455-67.
Scarborough et al., Aggregation of platelets by muscle actin. A multivalent interaction model of platelet aggregation by ADP. Biochem Biophys Res Commun. Jun. 16, 1981;100(3):1314-9.
Schroder et al., Lipoteichoic acid (LTA) of *Streptococcus pneumoniae* and *Staphylococcus aureus* activates immune cells via Toll-like receptor (TLR)-2, lipopolysaccharide-binding protein (LBP), and CD14, whereas TLR-4 and MD-2 are not involved. J Biol Chem. May 2, 2003;278(18):15587-94. Epub Feb. 19, 2003.
Schultz et al., Animal and human models for sepsis. Ann Med. 2002;34(7-8):573-81.
Semba et al., Low serum selenium is associated with anemia among older adults in the United States. Eur J Clin Nutr. Jan. 2009;63(1):93-9. Published online Sep. 5, 2007. doi: 10.1038/sj.ejcn.1602889.
Sheu et al., Mechanisms involved in the antiplatelet activity of *Escherichia coli* lipopolysaccharide in human platelets. Br J Haematol. Oct. 1998;103(1):29-38.
Shimazu et al., MD-2, A molecule that confers lipopolysaccharide responsiveness on Toll-like receptor 4. J Exp Med. Jun. 7, 1999;189(11):1777-82.
Simon et al., A matched crossover design for clinical trials. Contemp Clin Trials. Sep. 2007;28(5):638-46.
Smith et al., Decreased plasma gelsolin levels in patients with Plasmodium falciparum malaria: a consequence of hemolysis? Blood. Jul. 1988;72(1):214-8.
Smith et al., Evidence for two pathways of protein kinase C induction of 2ar expression: correlation with mitogenesis. J Cell Physiol. Apr. 1989;139(1):189-95.
Smith et al., Quantitative measurement of plasma gelsolin and its incorporation into fibrin clots. J Lab Clin Med. Aug. 1987;110(2):189-95.
Spudich et al., The regulation of rabbit skeletal muscle contraction. I. Biochemical studies of the interaction of the tropomyosin-troponin complex with actin and the proteolytic fragments of myosin. J Biol Chem. Aug. 10, 1971;246(15):4866-71.
Stossel, From signal to pseudopod. How cells control cytoplasmic actin assembly. J Biol Chem. Nov. 5, 1989;264(31):18261-4.
Suhler et al., Decreased plasma gelsolin concentrations in acute liver failure, myocardial infarction, septic shock, and myonecrosis. Crit Care Med. Apr. 1997;25(4):594-8.
Sun et al., Gelsolin, a multifunctional actin regulatory protein. J Biol Chem. Nov. 19, 1999;274(47):33179-82.
Tauber et al., Antibiotic therapy, endotoxin concentration in cerebrospinal fluid, and brain edema in experimental *Escherichia coli* meningitis in rabbits. J Infect Dis. Sep. 1987;156(3):456-62.
Thomas et al., Biopanning of endotoxin-specific phage displayed peptides. Biochem Biophys Res Commun. Jul. 18, 2003;307(1):133-8.
Tobias et al., Control of lipopolysaccharide-high-density lipoprotein interactions by an acute-phase reactant in human serum. Infect Immun. Oct. 1985;50(1):73-6.
Tobias et al., Isolation of a lipopolysaccharide-binding acute phase reactant from rabbit serum. J Exp Med. Sep. 1, 1986;164(3):777-93.
Trautner et al., Role of biofilm in catheter-associated urinary tract infection. Am J Infect Control. May 2004;32(3):177-83. doi: 10.1016/j.ajic.2003.08.005.
Tuominen et al., Fluorescent phosphoinositide derivatives reveal specific binding of gelsolin and other actin regulatory proteins to mixed lipid bilayers. Eur J Biochem. Jul. 1999;263(1):85-92.
Vasconcellos et al., Coordinated inhibition of actin-induced platelet aggregation by plasma gelsolin and vitamin D-binding protein. Blood. Dec. 15, 1993;82(12):3648-57.
Van Oosten et al., Scavenger receptor-like receptors for the binding of lipopolysaccharide and lipoteichoic acid to liver endothelial and Kupffer cells. J Endotoxin Res. 2001;7(5):381-4.
Villa et al., Pattern of cytokines and pharmacomodulation in sepsis induced by cecal ligation and puncture compared with that induced by endotoxin. Clin Diagn Lab Immunol. Sep. 1995;2(5):549-53.
Visapää et al., Correlation of Ki-67 and gelsolin expression to clinical outcome in renal clear cell carcinoma. Urology. Apr. 2003;61(4):845-50.
Vreugdenhil et al., Lipopolysaccharide (LPS)-binding protein mediates LPS detoxification by chylomicrons. J Immunol. Feb. 1, 2003;170(3):1399-405.
Walker et al., Enhanced Pseudomonas aeruginosa biofilm development mediated by human neutrophils. Infect Immun. Jun. 2005;73(6):3693-701.
Wang et al., HMG-1 as a late mediator of endotoxin lethality in mice. Science. Jul. 9, 1999;285(5425):248-51.
Wanner et al., Atorvastatin in patients with type 2 diabetes mellitus undergoing hemodialysis. N Engl J Med. Jul. 21, 2005;353(3):238-48.
Ware et al., The acute respiratory distress syndrome. N Engl J Med. May 4, 2000;342(18):1334-49.
Watson et al., Genetic control of responses to bacterial lipopolysaccharides in mice. II. A gene that influences a membrane component involved in the activation of bone marrow-derived lymphocytes by lipipolysaccharides. J Immunol. May 1975;114(5):1462-8.
Weiner et al., The antimicrobial activity of the cathelicidin LL37 is inhibited by F-actin bundles and restored by gelsolin. Am J Respir Cell Mol Biol. Jun. 2003;28(6):738-45. Epub Dec. 30, 2002.
Wen et al., The plasma and cytoplasmic forms of human gelsolin differ in disulfide structure. Biochemistry. Jul. 30, 1996;35(30):9700-9.
Witke et al., Hemostatic, inflammatory, and fibroblast responses are blunted in mice lacking gelsolin. Cell. Apr. 7, 1995;81(1):41-51.
Workeneh et al., Review of muscle wasting associated with chronic kidney disease. Am J Clin Nutr. Apr. 2010;91(4):1128S-1132S. Epub Feb. 24, 2010.
Yamamoto et al., Human plasma gelsolin binds adenosine triphosphate. J Biochem. Oct. 1990;108(4):505-6.

(56) References Cited

OTHER PUBLICATIONS

Yamamura et al., Sphingosine-1-phosphate inhibits actin nucleation and pseudopodium formation to control cell motility of mouse melanoma cells. FEBS Lett. Mar. 11, 1996;382(12):193-7.

Yancey et al., Risk factors for neonatal sepsis. Obstet Gynecol. Feb. 1996;87(2):188-94.

Yatomi, Sphingosine 1-phosphate in vascular biology: possible therapeutic strategies to control vascular diseases. Curr Pharm Des. 2006;12(5):575-87.

Yin et al., Structure and biosynthesis of cytoplasmic and secreted variants of gelsolin. J Biol Chem. Apr. 25, 1984;259(8):5271-6.

Zuo et al., [Bacteriological study of chronic sinusitis]. Zhonghua Er Bi Yan Hou Tou Jing Wai Ke Za Zhi. Jul. 2005;40(7):524-7. English Abstract.

* cited by examiner

USE OF GELSOLIN TO DIAGNOSE AND TREAT INFLAMMATORY DISEASES

RELATED APPLICATIONS

This application is a continuation of U.S. patent application Ser. No. 12/225,128, filed Mar. 22, 2010 (now U.S. Pat. No. 8,198,094), which is the U.S. National stage application of PCT International Application No. PCT/US2007/006451, filed Mar. 15, 2007. PCT International Application No. PCT/US2007/006451 claims the benefit under 35 U.S.C. §119(e) of U.S. Provisional Application No. 60/782,508, filed Mar. 15, 2006. The entire content of each of the foregoing applications is incorporated herein by reference.

FIELD OF THE INVENTION

The invention is directed to diagnostic and therapeutic uses of gelsolin.

BACKGROUND OF THE INVENTION

Inflammation is the body's response to injury, infection, or molecules perceived by the immune system as foreign. Inflammation is characterized by pain, swelling and altered function of the affected tissue. Although the ability to mount an inflammatory response is essential for survival, the ability to control inflammation is also necessary for health. Inflammatory diseases are characterized by activation of the immune system in a tissue or an organ to abnormal levels that may lead to abnormal function and/or disease in the tissue or organ.

Inflammatory diseases are a major cause of morbidity and mortality throughout the world. They affect various organs and tissues such as blood vessels, heart, brain, nerves, joints, skin, the lung, eye, gastrointestinal tract, kidneys, thyroid, adrenals, the pancreas, liver, and muscle. Treatments of inflammatory diseases have drawn a great deal of attention from the pharmaceutical industry. A recurrent theme in discussions of treatment options for inflammatory disorders is the inadequacy of the standard of care. Management and treatments are seeing improvements but there are no cures. The most common approach to treating inflammatory disorders in the last decade has addressed the pro-inflammatory role of cytokines with compounds that bind to these molecules or their receptors.

Despite recent advances, current therapies for inflammatory diseases still entail alleviating symptoms and reducing inflammation with non-specific drugs, slowing disease progression with disease-modifying agents, and improving the quality of life with lifestyle modifications, all while contending with side effects and resistance to medications. Better treatment options with less potential for side effects are needed.

Because the outcome of treatment depends on a proper diagnosis, it is important to have proper tests to diagnose inflammatory diseases and to monitor the treatment of those diseases. A proper diagnosis permits a physician to institute proper and timely therapy. Proper monitoring of treatment allows the physician to decide on the course of treatment and to advise patients and their families about the expected disease course. Thus, there is also a strong incentive to identify new improved tests and approaches to diagnose and to evaluate treatments of inflammatory diseases.

Gelsolin, first discovered as an intracellular actin-binding protein involved in cell motility (Yin, H. L. & Stossel, T. P. (1979) *Nature* 281, 583-6), has been recently implicated in a number of diseases. While the true function of plasma gelsolin is not known, clinical and animal studies have shown that depletion of plasma gelsolin by injury and inflammation is associated with adverse outcomes. The proposed mechanism of gelsolin depletion is that it binds abundant actin in cells exposed by tissue breakdown. More recently, gelsolin was found to bind bioactive inflammatory mediators, lysophosphatidic acid, diadenosine phosphate, Aβ peptide (a peptide implicated in the pathogenesis of Alzheimer's disease), platelet-activating factor and possibly others.

SUMMARY OF THE INVENTION

Gelsolin (GSN), specifically cytoplasmic gelsolin (cGSN), in addition to being an intracellular actin-binding protein involved in cell motility, is also an abundant secretory protein (Yin, H. L., Kwiatkowski, D. J., Mole, J. E. & Cole, F. S. (1984) *J Biol Chem* 259, 5271-6). The exported isoform of gelsolin, designated plasma gelsolin (pGSN), has 25 additional amino acids and originates from alternative splicing of a single gene (Kwiatkowski, D. J., Stossel, T. P., Orkin, S. H., Mole, J. E., Cohen, H. R. & Yin, H. L. (1986) *Nature* 323, 455-8).

This invention is based on the surprising discovery that plasma gelsolin levels are reduced in blood samples from human subjects with an inflammatory disease, rheumatoid arthritis (RA). These findings support the hypothesis that reductions in plasma gelsolin levels reflect the primary injury inflicted on joint tissues by the causative agency of rheumatoid arthritis and precede joint pain and destruction by the resultant inflammatory process. These observations provide a basis for treatment with gelsolin to prevent and/or suppresses the manifestations of inflammatory diseases. One correlate of these observations is that monitoring of plasma gelsolin levels could become part of the management strategy of rheumatoid arthritis.

Without intending to be bound by any particular mechanism or theory, it is believed that gelsolin might be exerting its protective effect by inhibiting mediators of inflammation. Thus, the invention is directed to methods of using gelsolin to diagnose inflammatory diseases and to monitor the effect of therapy. The invention also involves the use of gelsolin to treat inflammation and inflammatory diseases.

According to one aspect of the invention, a method for characterizing a subject's risk profile of developing a future inflammatory disease (e.g., rheumatoid arthritis in some preferred embodiments) is provided. The method comprises obtaining a level of gelsolin in the subject and comparing the level of the gelsolin to a predetermined value. The subject's risk profile of developing an inflammatory disease (e.g., rheumatoid arthritis) is characterized based upon the level of gelsolin in comparison to the predetermined value. A level of gelsolin at or below the predetermined level is indicative that the subject is at an elevated risk of developing the inflammatory disease and a level of gelsolin at or above the predetermined level is indicative that the subject is not at an elevated risk of developing the inflammatory disease.

In some embodiments, the method further comprises performing one or more tests to evaluate the inflammatory disease. Evaluating an inflammatory disease may involve measuring a level of a marker of inflammation in the subject. Examples of markers of inflammation include but are not limited to CRP, soluble intercellular adhesion molecule (sI-CAM-1), ICAM 3, BL-CAM, LFA-2, VCAM-1, NCAM, PECAM, fibrinogen, serum amyloid A (SAA), lipoprotein associated phospholipase A2 (LpP1A2), sCD40 ligand (sCD40L), myeloperoxidase, Interleukin-6 (IL-6), or Interleukin-8 (IL-8).

According to another aspect of the invention, a method for characterizing a subject's risk profile of developing a future inflammatory disease (e.g., rheumatoid arthritis in preferred embodiments) is provided. The method comprises obtaining a level of gelsolin in the subject and comparing the level of the gelsolin to a first predetermined value to establish a first risk value. A level of a second marker of inflammation in the subject is obtained and the level of the second marker of inflammation is compared to a second predetermined value to establish a second risk value. The subject's risk profile of developing the inflammatory disease is characterized based upon the combination of the first risk value and the second risk value, wherein the combination of the first risk value and second risk value establishes a third risk value different from said first and second risk values.

In some embodiments, the subject is an apparently healthy subject.

In some embodiments, the first predetermined value may be a plurality of predetermined gelsolin level ranges, one of a plurality of ranges being below about 250 mg/L of plasma and another of said ranges being above about 250 mg/L of plasma, and the comparing step comprises determining in which of said plurality of predetermined gelsolin level ranges said subject's gelsolin level falls.

According to another aspect of the invention, a method for treating a subject having or at risk of developing an inflammatory disease (e.g., rheumatoid arthritis in preferred embodiments) is provided. The method comprises administering an effective amount of gelsolin to the subject in need of such a treatment to treat the subject.

According to another aspect of the invention, a method for treating a subject having or at risk of developing an inflammatory disease (e.g., rheumatoid arthritis in preferred embodiments) is provided. The method comprises administering an effective amount of gelsolin to the subject in need of such a treatment to raise the level of gelsolin in the subject above a predetermined value.

In some embodiments, the subject is otherwise free of indications calling for treatment with gelsolin. The gelsolin preferably is administered orally, sublingually, buccally, intranasally, intravenously, intramuscularly, intraarticularly, intraperitoneally, subcutaneously, or topically. The gelsolin may be administered prophylactically.

In some embodiments, the treatment methods further comprise administering a second agent for treating the inflammatory disease (e.g., rheumatoid arthritis in preferred embodiments). Examples of agents for treating the inflammatory disease include but are not limited to Alclofenac, Alclometasone Dipropionate, Algestone Acetonide, Alpha Amylase, Ameinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Cyclooxygenase-2 (COX-2) inhibitor, Deflazacort, Desonide, Desoximetasone, Dexamethasone Dipropionate, Diclofenac Potassium, Diclofenac, Sodium, Diflorasone Diacetate, Diflumidone Sodium, Diflunisal, Difluprednate, Diftalone, Dimethyl Sulfoxide, Drocinonide, Endrysone, Enlimornab, Enolicam Sodium, Epirizole, Etodolac, Etofenamate, Felbinac, Fenamole, Fenbufen, Fenclofenac, Fenclorac, Fendosal, Fenpipalone, Fentiazac, Flozalone, Fluaza-cort, Flufenamic Acid, Flurnizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, or Zomepirac Sodium.

Anti-inflammatory agents also include Cyclooxygenase-2 (COX-2) inhibitors. Cyclooxygenase is an enzyme complex present in most tissues that produces various prostaglandins and thromboxanes from arachidonic acid. Non-steroidal, antiinflammatory drugs exert most of their antiinflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2, is rapidly and readily inducible by a number of agents including mitogens, endotoxin, hormones, cytokines and growth factors. As prostaglandins have both physiological and pathological roles, it is believed that the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar antiinflammatory, antipyretic and analgesic properties to a conventional non-steroidal antiinflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective COX-2 inhibitors are known in the art. Examples of selective COX-2 inhibitors include, for example, celecoxib (Celebrex®), valdecoxib (Bextra®) and rofecoxib (Vioxx®). Selective COX-2 inhibitors also include, but are not limited to, COX-2 inhibitors described in U.S. Pat. No. 5,474,995 "Phenyl heterocycles as COX-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

In some embodiments, the method further comprises administering a second agent for treating rheumatoid arthritis. Examples of agents for treating rheumatoid arthritis include but are not limited to hydroxychloroquine (Plaquenil), chloroquine (Aralen), methotrexate, sulfasalazine (Azulfidine), Leflunomide (Arava), azathioprine (Imuran), penicillamine (Cuprimine or Depen), Gold salts (Ridaura or Aurolate), minocycline (Dynacin or Minocin), cyclosporine (Neoral or Sandimmune) cyclophosphamide (Cytoxan or Neosar), Etanercept (Enbrel), Infliximab (Remicade), Ahakinra (Kineret) or Adalimumab (Humira).

According to another aspect of the invention, a method for treating a subject to reduce the risk of an inflammatory disease (e.g., rheumatoid arthritis in preferred embodiments) is provided. The method comprises selecting a subject on the basis that the subject is known to have a below-normal level of gelsolin and administering to the subject an effective amount of gelsolin and/or a second agent to reduce the risk of the subject developing the inflammatory disease (e.g., rheumatoid arthritis in preferred embodiments).

According to another aspect of the invention, a method for treating a subject to reduce the risk of an inflammatory disease (e.g., rheumatoid arthritis in preferred embodiments) is provided. The method comprises selecting a subject on the basis that the subject is known to have a below-normal level of gelsolin and administering an effective amount of gelsolin and/or a second agent to the subject to raise the level of gelsolin in the subject above a predetermined value.

In some embodiments, the method further comprises administering to the subject a second agent for treating the inflammatory disease (e.g., rheumatoid arthritis in preferred embodiments). Examples of agents for treating the inflammatory disease and rheumatoid arthritis are listed above.

According to yet another aspect of the invention, a method for treating a subject with a below-normal level of gelsolin is provided. The method comprises treating the subject with a first therapy for treating or reducing the risk of an inflammatory disease (e.g., rheumatoid arthritis in preferred embodiments). A level of gelsolin in the subject is obtained. The level of gelsolin is compared to a predetermined value corresponding to a predetermined level of gelsolin (e.g., in an apparently healthy control population). If the predetermined level of gelsolin is not reached, the subject is treated with a second agent for treating or reducing the risk of the inflammatory disease (e.g., rheumatoid arthritis in preferred embodiments) until the predetermined level of gelsolin is reached.

A "below-normal level of gelsolin" is a gelsolin level is at least 10% less than the measured mean level for a given population of subjects. The mean gelsolin level can depend upon the particular population of subjects. For example, an apparently healthy population will have a different "normal" range of gelsolin than will a population of subjects which have had a prior condition. In some embodiments, the gelsolin level is at least 10% less than the measured mean level for a given population of subjects. In other embodiments, the gelsolin level is at least 20% less than the measured mean level for a given population of subjects. In still other embodiments, the gelsolin level is at least 30%, 40%, 50%, 60%, 70%, 80%, 90%, 95%, 99% or 100% less than the measured mean level for a given population of subjects. In one of the embodiments, the gelsolin level is below about 250 mg/L of plasma. In other important embodiments, the gelsolin level is below about 2.4 µM/L (micromoles/Liter) of plasma.

In some embodiments the subject is otherwise free of indications calling for treatment with the agent. When the agent is gelsolin, a subject free of indications calling for treatment with gelsolin is a subject who has no signs or symptoms calling for treatment with gelsolin. Gelsolin is indicated for the treatment of sepsis and infections. Gelsolin is also indicated for the treatment of actin-related disorders such as Adult Respiratory Distress Syndrome (ARDS), fulminant hepatic necrosis, acute renal failure, muscle injury, disorders characterized by elevated levels of BUN and/or creatinine. Actin-related disorders are known to those of ordinary skill in the art.

In other embodiments, the subject is apparently healthy. As used herein an "apparently healthy subject" is a subject who has no signs and/or symptoms of a disease.

According to another aspect of the invention, a method for evaluating the efficacy of a therapy for treating or reducing the risk of an inflammatory disease (e.g., rheumatoid arthritis in preferred embodiments) in a subject is provided. The method comprises obtaining a level of gelsolin in a subject undergoing therapy with an agent to treat or reduce the risk of inflammatory disease (e.g., rheumatoid arthritis in preferred embodiments). The level of gelsolin obtained is compared to a predetermined value corresponding to a level of gelsolin (e.g., in an apparently healthy control population). A determination of whether the level of gelsolin is above the predetermined level is indicative of whether the therapy is efficacious. In some embodiments, obtaining a level of the gelsolin is repeated so as to monitor the subject's level of the gelsolin over time.

The therapy may be with gelsolin, Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Cyclooxygenase-2 (COX-2) inhibitor, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin. Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenarnic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Zomepirac Sodium, hydroxychloroquine (Plaquenil), chloroquine (Aralen), methotrexate, sulfasalazine (Azulfidine), Leflunomide (Arava), azathioprine (Imuran), penicillamine (Cuprimine or Depen), Gold salts (Ridaura or Aurolate), minocycline (Dynacin or Minocin), cyclosporine (Neoral or Sandimmune) cyclophosphamide (Cytoxan or Neosar), Etanercept (Enbrel), Infliximab (Remicade), Anakinra (Kineret) or Adalimurnab (Humira).

According to still another aspect of the invention, a method for deciding on the course of a therapy in a subject is provided. The method comprises obtaining a level of gelsolin in a subject undergoing a therapy to treat or reduce the risk of an inflammatory disease (e.g., rheumatoid arthritis in preferred embodiments). The level of gelsolin is compared to a predetermined value corresponding to a level of gelsolin (e.g., in an apparently healthy control population). Whether the level of gelsolin obtained is at or above or at or below the predetermined level is determined and the course of therapy is decided based on such determination. In some embodiments, obtaining a level of gelsolin is repeated so as to monitor the subject's level of gelsolin over time.

The following embodiments apply to various aspects of the invention set forth herein unless indicated otherwise.

The inflammatory disease may be arthritis, rheumatoid arthritis, asthma, inflammatory bowel disease (Crohn's disease or ulcerative colitis), chronic obstructive pulmonary disease (COPD), allergic rhinitis, vasculitis (polyarteritis nodosa, temporal arteritis, Wegener's granulomatosus, Takayasu's arteritis, or Behcet syndrome), inflammatory neuropathy, psoriasis, systemic lupus erythematosis (SLE), chronic thyroiditis, Hashimoto's thyroiditis, Addison's disease, polymyalgia rheumatica, Sjogren's syndrome, or Churg-Strauss syndrome. In some important embodiments, the inflammatory disease is rheumatoid arthritis.

The level of gelsolin may be in a body fluid of the subject. Examples of body fluids include but are not limited to blood, plasma, serum, urine, synovial fluid, or alveolar fluid.

The level of gelsolin may be in a body tissue of the subject. The body tissue may be joint, gastrointestinal, thyroid, adrenal, vascular, pulmonary, renal, cardiac, skin, ocular, brain pancreatic, liver, nerve, or muscle tissue. In some embodiments, the subject is an apparently healthy subject.

In some embodiments, the predetermined value is 250 mg/L of plasma or lower. In some embodiments, the predetermined value of gelsolin is about 240 mg/L, 230 mg/L, 220 mg/L, 210 mg/L, 200 mg/L, 190 mg/L, 180 mg/L, 170 mg/L, 160 mg/L, 150 mg/L, 140 mg/L, 130 mg/L, 120 mg/L, 110 mg/L, 100 mg/L, 90 mg/L, 80 mg/L, 70 mg/L, 60 mg/L, 50 mg/L, 40 mg/L, 30 mg/L, 20 mg/L, or 10 mg/L of plasma or lower.

In some other embodiments, the predetermined value is 2.4 µM/L of plasma or lower. In some embodiments, the predetermined value of gelsolin is about 2.3 µM/L, 2.2 µM/L, 2.1 µM/L, 2.0 µM/L, 1.9 µM/L, 1.8 µM/L, 1.7 µM/L, 1.6 µM/L, 1.5 µM/L, 1.4 µM/L, 1.3 µM/L, 1.2 µM/L, 1.1 µM/L, 1.0 µM/L, 0.9 µM/L, 0.8 µM/L, 0.7 µM/L, 0.6 µM/L, 0.5 µM/L, 0.4 µM/L, 0.3 µM/L, 0.2 µM/L of plasma or lower.

Each of the limitations of the invention can encompass various embodiments of the invention. It is, therefore, anticipated that each of the limitations of the invention involving any one element or combinations of elements can be included in each aspect of the invention. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description of the Invention. Each aspect of the invention can encompass various embodiments as will be understood.

Figure 1:
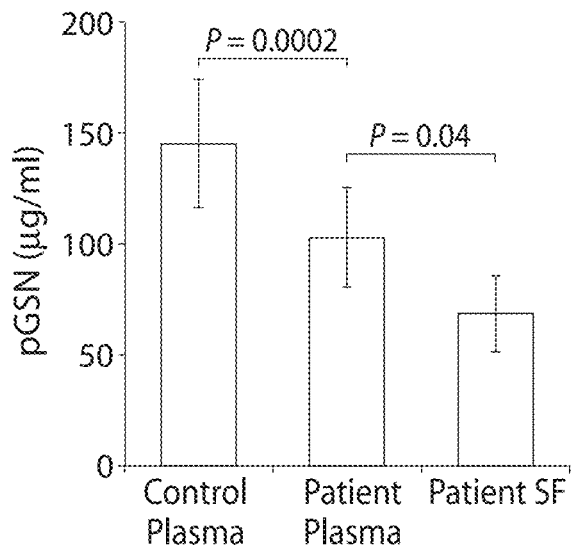
FIG. 1 is a histogram showing that plasma gelsolin (pGSN) concentration is decreased in patients with rheumatoid arthritis (RA) compared to healthy controls and lower in synovial fluid than in blood in patients with RA.

It is to be understood that the drawings are not required for enablement of the invention.

DETAILED DESCRIPTION OF THE INVENTION

This invention is based on the surprising discovery that plasma gelsolin levels are reduced in blood samples from human subjects with an inflammatory disease, rheumatoid arthritis (RA). It is hypothesized that plasma gelsolin levels fall in response to the initial (unknown) injury inflicted by the agency causing RA. Therefore, peripheral gelsolin replacement can ameliorate the secondary injury mediated by various inflammatory cells. It is believed that the pattern of gelsolin depletion to predict disease and the use of gelsolin to treat disease is true for inflammatory diseases in general.

Thus, the invention involves, in some aspects, administering gelsolin to a subject to treat an inflammatory disease in the subject. The term "treat" or "treatment" is intended to include prophylaxis, amelioration, prevention or cure from the disease.

As used herein the term "subject" means any mammal that may be in need of treatment. Subjects include but are not limited to: humans, non-human primates, cats, dogs, sheep, pigs, horses, cows, rodents such as mice, hamsters, and rats. Preferred subjects are human subjects.

As used herein the term "gelsolin" encompasses wild type gelsolin (GenBank accession No.: X04412), isoforms, analogs, variants, fragments or functional derivatives of gelsolin.

Gelsolin (GSN), unlike other mammalian proteins, has both cytoplasmic (cGSN) and secreted or exported isoforms, also called plasma gelsolin (pGSN), which are derived by alternative splicing of the message from a single gene (Sun et al. *J. Biol. Chem.* 274:33179-33182 (1999)). As used herein, gelsolin isoforms include versions of gelsolin with some small differences in their amino acid sequences, usually a splice variant or the result of some posttranslational modification.

Gelsolin encompasses native as well as synthetic and recombinant gelsolin and gelsolin analogs. Gelsolin is an abundant secretory protein (Yin, H. L., Kwiatkowski, D. J., Mole, J. E. & Cole, F. S. (1984) *J Biol Chem* 259, 5271-6). The exported isoform of gelsolin, pGSN, has 25 additional amino acids and originates from alternative splicing of a single gene (Kwiatkowski, D. J., Stossel, T. P., Orkin, S. H., Mole, J. E., Cohen, H. R. & Yin, H. L. (1986) *Nature* 323, 455-8). Recombinant human gelsolin (rhGSN) (Biogen IDEC, Inc., Cambridge, Mass.) is produced in *E. coli*, and though it has the same primary structure as the native protein, under standard conditions of purification, it differs from natural human plasma gelsolin by a disulfide bond that is present in the natural protein. The recombinant protein is, therefore, properly oxidized after purification, and its structure and functions are indistinguishable from human plasma gelsolin (Wen et. al., *Biochemistry* 35:9700-9709 (1996)). In some of the important therapeutic aspects and embodiments of the invention, the use of rhGSN is preferred. In some of the important diagnostic aspects and embodiments of the invention, the use of pGSN is preferred.

A "gelsolin analog" refers to a compound substantially similar in function to either the native gelsolin or to a fragment thereof. Gelsolin analogs include biologically active amino acid sequences substantially similar to the gelsolin sequences and may have substituted, deleted, elongated, replaced, or otherwise modified sequences that possess bioactivity substantially similar to that of gelsolin. For example, an analog of gelsolin is one which does not have the same amino acid sequence as gelsolin but which is sufficiently homologous to gelsolin so as to retain the bioactivity of gelsolin. Bioactivity can be determined, for example, by determining the properties of the gelsolin analog and/or by determining the ability of the gelsolin analog to treat or prevent rheumatoid arthritis. One example of a gelsolin bioactivity assay is gelsolin's ability to stimulate actin nucleation. Gelsolin bioactivity assays are described in the Example and are known to those of ordinary skill in the art.

A "fragment" is meant to include any portion of a gelsolin molecule which provides a segment of gelsolin which maintains the bioactivity of gelsolin; the term is meant to include gelsolin fragments which are made from any source, such as, for example, from naturally-occurring peptide sequences, synthetic or chemically-synthesized peptide sequences, and genetically engineered peptide sequences.

A "variant" of gelsolin is meant to refer to a compound substantially similar in structure and bioactivity either to native gelsolin, or to a fragment thereof. The term variant encompasses the gelsolin family of proteins. The gelsolin family of proteins is a group of actin binding proteins sharing repeats of about 15 kDa homologous domains that adopt a similar fold. Examples gelsolin family proteins include but are not limited to advillin, villin, capG, flightless proteins, fragmin, severin, adseverin, protovillin, and supervillin.

A "functional derivative" of gelsolin is a derivative which possesses a bioactivity that is substantially similar to the bioactivity of gelsolin. By "substantially similar" is meant activity which is quantitatively different but qualitatively the same. For example, a functional derivative of gelsolin could contain the same amino acid backbone as gelsolin but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of gelsolin. Such derivatives may improve gelsolin's solubility, absorption, biological half life, etc. The derivatives may also decrease the toxicity of gelsolin, or eliminate or attenuate any undesirable side effect of gelsolin, etc. Chemical moieties capable of mediating such effects are disclosed in Remington's Pharmaceutical Sciences (1980). Procedures for coupling such moieties to a molecule such as gelsolin are well known in the art. The term "functional derivative" is intended to include the "fragments," "variants," "analogues," or "chemical derivatives" of gelsolin.

The invention involves in some aspects, methods for treating an inflammatory disease (e.g., rheumatoid arthritis in preferred embodiments) in a subject. The subject is known to have, is suspected of having, or is at risk of having the inflammatory disease. The gelsolin is administered in an amount effective to treat the inflammatory disease in the subject.

A response to a treatment method of the invention can, for example, be measured by determining the physiological effects of the treatment, such as the decrease or lack of symptoms following administration of the treatment.

In another aspect of the invention, a method for monitoring therapy in a subject is provided. The method involves obtaining a level of gelsolin in a subject undergoing therapy to treat an inflammatory disease (e.g., rheumatoid arthritis in preferred embodiments). The level of gelsolin is compared to a predetermined value corresponding to a control level of gelsolin (e.g., in an apparently healthy population). A determination of whether the level of gelsolin is at or below a predetermined level is indicative of whether the subject would benefit from continued therapy with the same therapy or would benefit from a change in therapy. In some embodiments, obtaining a level of gelsolin is repeated so as to monitor the subject's levels of gelsolin over time. In some embodiments, the subject may have been undergoing the therapy for at least 1, 2, 3, 4, 5, 6, 7, 8, 9, 10, 11, 12 weeks or more. In some embodiments, the subject may have been undergoing the therapy for at least 3, 4, 5, 6 months, or more.

A change in therapy with gelsolin refers to an increase in the dose of the gelsolin, a switch from one gelsolin to another gelsolin, a switch from gelsolin to another agent, the addition of another agent to the gelsolin therapeutic regimen, or a combination thereof.

According to another aspect of the invention, a method for evaluating the efficacy of a therapy for treating or reducing the risk of an inflammatory disease (e.g., rheumatoid arthritis in preferred embodiments) is provided. The method involves obtaining a level of gelsolin in a subject undergoing therapy to treat the inflammatory disease. The level of gelsolin is compared to a predetermined value corresponding to a control level of gelsolin (e.g., in an apparently healthy population). A determination that the level of gelsolin is at or above a predetermined level is indicative that the therapy is efficacious. In some embodiments, the subject may have been undergoing the therapy for at least at least 1, 2, 3, 4, 5, 6, 7, 8, 9, 10, 11, 12 weeks or more. In some embodiments, the subject may have been undergoing the therapy for at least 3, 4, 5, 6 months, or more.

One aspect of the invention is directed to the measurement of gelsolin to guide treatments in order to improve outcome in subjects. On-therapy levels of gelsolin have predictive value for response to treatments of an inflammatory disease (e.g., rheumatoid arthritis in preferred embodiments). The on-therapy levels of gelsolin are additive to prior art predictors of outcome of the disease.

Subjects who would benefit from this aspect of this invention are subjects who are undergoing therapy to treat or prevent the inflammatory disease such as, for example, rheumatoid arthritis (i.e., a subject "on-therapy"). A subject on-therapy is a subject who already has been diagnosed and is in the course of treatment with a therapy for treating an inflammatory disease such as rheumatoid arthritis. The therapy can be any of the therapeutic agents referred to herein. The therapy also can be non-drug treatments. In important embodiments, the therapy is one which increases levels of gelsolin. In a particularly important embodiment, the therapy is a therapy with gelsolin. Preferred subjects are human subjects. The subject most likely to benefit from this invention is a human subject on-therapy and who has a gelsolin level at or below about 250 mg/L (or 2.4 µM/L) of plasma.

In some embodiments, the subject already has the disease. In some embodiments, the subject may be at an elevated risk of having the disease.

Risk factors for diseases are known to those of ordinary skill in the art. For example, risk factors for rheumatoid arthritis include: age (between 25 and 45 years), female gender, Caucasian or native American ethnicity, obesity, and a positive family history. The degree of risk of rheumatoid arthritis depends on the multitude and the severity or the magnitude of the risk factors that the subject has. Risk charts and prediction algorithms are available for assessing the risk of inflammatory diseases such as rheumatoid arthritis in a subject based on the presence and severity of risk factors. In some embodiments, the subject who is at an elevated risk of having the inflammatory disease may be an apparently healthy subject. An apparently healthy subject is a subject who has no signs or symptoms of disease.

Other methods of assessing the risk of an inflammatory disease in a subject are known by those of ordinary skill in the art.

The preferred treatment of the instant invention is gelsolin. Gelsolin may be administered alone, in a pharmaceutical composition or combined with other therapeutic regimens. Gelsolin and optionally other therapeutic agent(s) may be administered simultaneously or sequentially. When the other therapeutic agents are administered simultaneously they can be administered in the same or separate formulations, but are administered at the same time. The other therapeutic agents may be administered sequentially with one another and with gelsolin when the administration of the other therapeutic agents and the gelsolin is temporally separated. The separation in time between the administration of these compounds may be a matter of minutes or it may be longer.

In practicing certain methods of the present invention, it is required to obtain a level of gelsolin in a subject. This level then is compared to a predetermined value, wherein the level of gelsolin in comparison to the predetermined value is indicative of the likelihood that the subject will benefit from continued therapy. The subject then can be characterized in terms of the net benefit likely to be obtained from a change in therapy.

The level of the gelsolin for the subject can be obtained by any art recognized method. Typically, the level is determined by measuring the level of gelsolin in a body fluid, for example, blood, serum, plasma, lymph, saliva, urine, synovial fluid and the like. The level can be determined by ELISA, or other immunoassays or other conventional techniques for determining the presence of gelsolin. Conventional methods may include sending a sample(s) of a subject's body fluid to a commercial laboratory for measurement. Methods for measuring gelsolin are described in the Example.

The invention also involves comparing the level of gelsolin for the subject with a predetermined value. The predetermined value can take a variety of forms. It can be single cut-off value, such as a median or mean. It can be established based upon comparative groups, such as, for example, where the risk in one defined group is double the risk in another defined group. It can be a range, for example, where the tested population is divided equally (or unequally) into groups, such as a low-risk group, a medium-risk group and a high-risk group, or into quartiles, the lowest quartile being subjects with the highest risk and the highest quartile being subjects with the lowest risk, or into tertiles the lowest tertile being subjects with the highest risk and the highest tertile being subjects with the lowest risk. The predetermined value may be a cut-off value which is predetermined by the fact that a group having a gelsolin level no less than the cut-off value demonstrates a statistically significant increase in the risk of developing an inflammatory disease (e.g., rheumatoid arthritis in preferred embodiments) as compared to a comparative group. In some embodiments the comparative group is a group having a lower level of gelsolin.

The predetermined value can depend upon the particular population of subjects selected. For example, an apparently healthy population may have a different 'normal' range of gelsolin than will populations of subjects which have other conditions. Accordingly, the predetermined values selected may take into account the category in which a subject falls. Appropriate ranges and categories can be selected with no more than routine experimentation by those of ordinary skill in the art. The preferred body fluid is blood. In some embodiments, the predetermined value of gelsolin is about 250 mg/L of plasma or lower. In some embodiments, the predetermined value of gelsolin is about 240 mg/L, 230 mg/L, 220 mg/L, 210 mg/L, 200 mg/L, 190 mg/L, 180 mg/L, 170 mg/L, 160 mg/L, 150 mg/L, 140 mg/L, 130 mg/L, 120 mg/L, 110 mg/L, 100 mg/L, 90 mg/L, 80 mg/L, 70 mg/L, 60 mg/L, 50 mg/L, 40 mg/L, 30 mg/L, 20 mg/L, or 10 mg/L of plasma or lower. In some embodiments, the predetermined value of gelsolin is about 2.4 µM/L of plasma or lower. In some embodiments, the predetermined value of gelsolin is about 2.3 µM/L, 2.2 µM/L, 2.1 µM/L, 2.0 µM/L, 1.9 µM/L, 1.8 µM/L, 1.7 µM/L, 1.6 µM/L, 1.5 µM/L, 1.4 µM/L, 1.3 µM/L, 1.2 µM/L, 1.1 µM/L, 1.0 µM/L, 0.9 µM/L, 0.8 µM/L, 0.7 µM/L, 0.6 µM/L, 0.5 µM/L, 0.4 µM/L, 0.3 µM/L, 0.2 µM/L of plasma or lower.

An important predetermined value of gelsolin is a value that is the average for a healthy subject population (i.e., subjects who have no signs and symptoms of disease). The predetermined value will depend, of course, upon the characteristics of the subject population in which the subject lies. In characterizing risk, numerous predetermined values can be established.

Presently, there are commercial sources which produce reagents for assays for gelsolin. These include, for example, Cytoskeleton (Denver, Colo.), Sigma (St. Louis, Mo.) and Calbiochem (San Diego, Calif.)

In some embodiments, the invention further comprises measuring the level of gelsolin together with a level of a second marker of an inflammatory disease (e.g., rheumatoid arthritis in preferred embodiments). Markers for inflammatory diseases are known to those of ordinary skill in the art and examples of which are described above. Examples of markers for rheumatoid arthritis include, for example, anti cyclic citrullinated peptide (anti-CCP) antibodies, HLA-DR4, and C-reactive protein (CRP). A level of gelsolin in the subject is obtained. The level of gelsolin is compared to a predetermined value to establish a first risk value. A level of the second marker inflammatory disease in the subject is also obtained. The level of the second marker inflammatory disease in the subject is compared to a second predetermined value to establish a second risk value. The subject's risk profile of developing the inflammatory disease (e.g., rheumatoid arthritis in preferred embodiments) then is characterized based upon the combination of the first risk value and the second risk value, wherein the combination of the first risk value and second risk value establishes a third risk value different from the first and second risk values. In some embodiments, the third risk value is greater than either of the first and second risk values. The preferred subjects for testing and predetermined values are as described above. The disease may be any of the inflammatory disease described above.

The invention provides methods for determining whether a subject will benefit from continued therapy or would benefit from a change in therapy. The benefit is typically a reduction in the signs and symptoms or a faster recovery from the manifestations of the disease. Signs, symptoms and manifestations of disease are known to those of ordinary skill in the art. For example, in rheumatoid arthritis, signs and symptoms of the disease include pain, swelling and tenderness in the affected joint(s).

These methods have important implications for patient treatment and also for the clinical development of new therapies. Determining whether a subject will benefit from continued therapy or would benefit from a change in therapy is clinically useful. One example of clinical usefulness of the methods of this invention includes identifying subjects who are less likely or more likely to respond to a therapy. The methods of the invention are also useful in predicting or determining that a subject would benefit from continued therapy or would benefit from a change in therapy. Health care practitioners select therapeutic regimens for treatment based upon the expected net benefit to the subject. The net benefit is derived from the risk to benefit ratio. The present invention permits the determination of whether a subject will benefit from continued therapy or would benefit from a change in therapy, thereby aiding the physician in selecting a therapy.

Another example of clinical usefulness, in the case of human subjects for example, includes aiding clinical investigators in the selection for clinical trials of subjects with a high likelihood of obtaining a net benefit. It is expected that clinical investigators now will use the present invention for determining entry criteria for clinical trials.

A subject who would benefit from continued therapy is a subject whose on-therapy level of gelsolin reaches a certain predetermined value or whose level of gelsolin is increasing. Predetermined values of gelsolin are described above. A subject who would benefit from a change in therapy is a subject whose on-therapy level of the gelsolin did not reach a certain predetermined value or whose on-therapy level of gelsolin is not increasing.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. In some embodiments, preferred therapies are therapies that increase the levels of gelsolin. A subject who would benefit from a change in therapy by increasing the dose of the existing therapy is a subject who, for example, was on the therapy but was not receiving the maximum tolerated dose or the maximum allowed dose of the therapy and whose level of gelsolin did not reach a certain predetermined value. In such instances the dose of the existing therapy is increased until the level of gelsolin reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. A subject who would benefit from a change in therapy by decreasing the dose of the existing therapy is, for example, a subject whose on-therapy level of gelsolin reaches or can reach a certain predetermined value with a lower dose of the therapy.

A subject who would benefit from a switch from one therapy to another therapy is, for example, a subject who was on the maximum tolerated dose or the maximum allowed dose of the therapy and whose level of gelsolin did not reach a certain predetermined value. Another example is a subject was not on the maximum tolerated or the maximum allowed dose of the therapy but was determined by a health care practitioner to more likely benefit from another therapy. Such determinations are based, for example, on the development in the subject of unwanted side effects on the initial therapy or a lack of response to the initial therapy.

A subject who would benefit from a change in therapy by the addition of another therapy to the existing therapy is, for example, a subject who was on a therapy but whose level of gelsolin did not reach a certain predetermined value. In such instances, another therapy is added to the existing therapy. The therapy that is added to the existing therapy can have a different mechanism of action in increasing the level of gelsolin than the existing therapy. In some instances, a combination of the aforementioned changes in therapy may be used.

The invention also provides methods for determining the efficacy of a therapy. The efficacy is typically the efficacy of the therapy in increasing the level of gelsolin. This is sometimes also referred to as a positive response or a favorable response. Efficacy can be determined by a gelsolin blood test(s) to determine whether gelsolin levels are increased as a result of therapy. In some embodiments efficacy determination is based on the efficacy of a therapy in increasing both gelsolin and normalizing levels of markers of inflammation and/or normalizing white blood cell (WBC) counts.

The gelsolin measurement is typically reported in µM/L (micromoles/Liter), mg/dl (milligrams/deciliter), or mg/L (milligrams/Liter).

The invention also provides methods for deciding on the course of a therapy in a subject undergoing therapy for an inflammatory disease such as rheumatoid arthritis. Such a course of therapy is decided on the basis of the level of gelsolin. In some embodiments, the subject already has the disease or is at risk of having the inflammatory disease. In some embodiments, the subject is at an elevated risk of having the inflammatory disease the subject has one or more risk factors to have the disease.

The amount of a treatment may be varied for example by increasing or decreasing the amount of gelsolin or pharmacological agent or a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and like factors are within the knowledge and expertise of the health practitioner. For example, an effective amount can depend upon the duration the individual has had the inflammatory disease.

An effective amount is a dosage of the therapeutic agent sufficient to provide a medically desirable result. An effective amount may also, for example, depend upon the degree to which an individual has abnormally decreased levels of gelsolin. It should be understood that the therapeutic agents of the invention are used to treat or prevent the inflammatory disease (such as rheumatoid arthritis), that is, they may be used prophylactically in subjects at risk of developing the inflammatory disease (such as rheumatoid arthritis). Thus, an effective amount is that amount which can lower the risk of, slow or perhaps prevent altogether the development of the inflammatory disease (such as rheumatoid arthritis). It will be recognized when the therapeutic agent is used in acute circumstances, it is used to prevent one or more medically undesirable results that typically flow from such adverse events.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to treat the inflammatory disease. For example, in the case of rheumatoid arthritis, the desired response is inhibiting the progression of rheumatoid arthritis. This may involve only slowing the progression of rheumatoid arthritis temporarily, although more preferably, it involves halting the progression of the rheumatoid arthritis permanently. This can be monitored by routine diagnostic methods known to those of ordinary skill in the art. The desired response to treatment of rheumatoid arthritis also can be delaying the onset or even preventing the onset of rheumatoid arthritis.

The pharmacological agents used in the methods of the invention are preferably sterile and contain an effective amount of gelsolin for producing the desired response in a unit of weight or volume suitable for administration to a subject. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg, preferably from about 0.1 mg/kg to about 500 mg/kg, and most preferably from about 0.2 mg/kg to about 250 mg/kg, in one or more dose administrations daily, for one or more days.

Gelsolin and optionally other therapeutics may be administered per se or in the form of a pharmaceutically acceptable salt.

Various modes of administration are known to those of ordinary skill in the art which effectively deliver the pharmacological agents of the invention to a desired tissue, cell, or bodily fluid. The administration methods are discussed elsewhere in the application. The invention is not limited by the particular modes of administration disclosed herein. Standard references in the art (e.g., *Remington's Pharmaceutical Sciences,* 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride, chlorobutanol, parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle (e.g., saline, buffer, or sterile pyrogen-free water) before use.

Compositions suitable for oral administration may be presented as discrete units, such as capsules, tablets, pills, lozenges, each containing a predetermined amount of the active compound (e.g., gelsolin). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, sorbitol or cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of gelsolin or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, gelsolin may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of gelsolin either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of gelsolin. Gelsolin is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products; including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of gelsolin. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified gelsolin may also be prepared in different formulations depending on the type of chemical modification or the type of device employed.

Formulations suitable for use with a nebulizer, either jet or ultrasonic, will typically comprise gelsolin dissolved in water at a concentration of about 0.1 to 25 mg of biologically active gelsolin per mL of solution. The formulation may also include a buffer and a simple sugar (e.g., for gelsolin stabilization and regulation of osmotic pressure). The nebulizer formulation may also contain a surfactant, to reduce or prevent surface induced aggregation of the gelsolin caused by atomization of the solution in forming the aerosol.

Formulations for use with a metered-dose inhaler device will generally comprise a finely divided powder containing the gelsolin suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing gelsolin and may also include a bulking agent, such as lactose, sorbitol, sucrose, or mannitol in amounts which facilitate dispersal of the powder from the device, e.g., 50 to 90% by weight of the formulation. The gelsolin should most advantageously be prepared in particulate form with an average particle size of less than 10 mm (or microns), most preferably 0.5 to 5 mm, for most effective delivery to the distal lung.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic agent(s), including specifically but not limited to gelsolin, may be provided in particles. Particles as used herein means nano or microparticles (or in some instances larger) which can consist in whole or in part of gelsolin or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the gelsolin in a solution or in a semi-solid state. The particles may be of virtually any shape.

Both non-biodegradable and biodegradable, polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. F. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

For topical administration to the eye, nasal membranes, mucous membranes or to the skin, the gelsolin may be formulated as ointments, creams or lotions, or as a transdermal patch or intraocular insert or iontophoresis. For example, ointments and creams can be formulated with an aqueous or oily base alone or together with suitable thickening and/or gelling agents. Lotions can be formulated with an aqueous or oily base and, typically, further include one or more emulsifying agents, stabilizing agents, dispersing agents, suspending agents, thickening agents, or coloring agents. (See, e.g., U.S. Pat. No. 5,563,153, entitled "Sterile Topical Anesthetic Gel", issued to Mueller, D., et al., for a description of a pharmaceutically acceptable gel-based topical carrier.)

In general, the gelsolin is present in a topical formulation in an amount ranging from about 0.01% to about 30.0% by weight, based upon the total weight of the composition. Preferably, the gelsolin is present in an amount ranging from about 0.5 to about 30% by weight and, most preferably, the gelsolin is present in an amount ranging from about 0.5 to about 10% by weight. In one embodiment, the compositions of the invention comprise a gel mixture to maximize contact with the surface of the localized pain and minimize the volume and dosage necessary to alleviate the localized pain. GELFOAM® (a methylcellulose-based gel manufactured by Upjohn Corporation) is a preferred pharmaceutically acceptable topical carrier. Other pharmaceutically acceptable carriers include iontophoresis for transdermal drug delivery.

The invention also contemplates the use of kits. In some aspects of the invention, the kit can include a pharmaceutical preparation vial, a pharmaceutical preparation diluent vial, and gelsolin. The vial containing the diluent for the pharmaceutical preparation is optional. The diluent vial contains a diluent such as physiological saline for diluting what could be a concentrated solution or lyophilized powder of gelsolin. The instructions can include instructions for mixing a particular amount of the diluent with a particular amount of the concentrated pharmaceutical preparation, whereby a final formulation for injection or infusion is prepared. The instructions may include instructions for treating a subject with an effective amount of gelsolin. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Plasma gelsolin (pGSN) is a secreted protein that circulates in the extracellular fluids of humans at concentrations averaging 250 mg/l. Diverse types of tissue injury lead to prolonged reductions in plasma gelsolin levels. Following severe tissue injury encountered in severe trauma, burns, sepsis, major surgery and hematopoietic stem cell transplant patients, declines in gelsolin (GSN) levels to approximately less than 25% of normal precede and, therefore, predict critical care complications measured by assisted ventilation requirements, length of intensive care unit residence and overall hospital stays, death and specific sequelae such as secondary lung injury (e.g. adult respiratory distress syndrome (ARDS), acute lung injury (ALI), multiple organ dysfunction syndromes (MODS)). Similar plasma gelsolin reductions in animal models precede lung permeability changes and inflammation, and infusion of recombinant plasma gelsolin ameliorates these effects.

Example 1

Plasma Gelsolin (pGSN) Concentration is Decreased in Patients with Rheumatoid Arthritis (RA) Compared to Healthy Controls and Lower in Synovial Fluid than in Blood in Patients with RA We measured plasma gelsolin (pGSN) levels in patients with rheumatoid arthritis (RA) to experimentally test the hypothesis that plasma gelsolin levels fall in response to the initial (unknown) injury inflicted by the agency causing rheumatoid arthritis. As shown in FIG. 1, circulating (pGSN) levels were significantly lower in patients with RA compared to matched healthy controls (103±23 versus 142±29, P=0.0002, FIG. 1). pGSN levels were similar in both male and females, and were not dependent on the age of the patients or on the duration of arthritis. Circulating pGSN levels were inversely correlated to the levels of C-reactive protein (r=−0.272, p=0.026).

Materials and Methods:

Patients: Plasma and synovial fluid samples were collected from 82 RA patients attending the Rheumatology clinics, at Sahlgrenska University Hospital in Gothenburg, for acute joint effusion. RA was diagnosed according to the American College of Rheumatology criteria. At the time of synovial fluid and blood sampling all the patients received non-steroidal anti-inflammatory drugs. Recent radiographs of the hands and feet were obtained for all the patients. Presence of bone erosions defined as the loss of cortical definition of the joint, was recorded in proximal interphalangeal, metacarpophalangeal, carpus, interphalangeal and metatarsophalangeal joints of forefeet. Presence of one erosion was sufficient to fulfil requirement of an erosive disease. Presence of rheumatoid factor of any of immunoglobulin isotypes tested (IgM, -A, -G) was considered as positive. Control blood samples (n=87) were obtained from the blood donors attending Blood Transfusion Unit of Sahlgrenska University Hospital and matching the RA patients for age and gender.

Collection and preparation of samples: Synovial fluid was obtained from knee joints by arthrocentesis, aseptically aspirated and transferred into sodium citrate (0.129 mol/l; pH 7.4) containing tubes. Blood samples were simultaneously obtained from the cubital vein and collected into sodium citrate medium. Collected blood and synovial fluid samples were centrifuged at 800 g for 15 minutes, aliquoted, and stored frozen at −70° C. until use.

Measurement of pGSN concentration in plasma and synovial fluid by pyrene actin-nucleation assay: pGSN is activated by calcium and binds two actin monomers to form a nucleus from which actin polymerizes in pointed (slowest growing) end direction. Pyrene actin was prepared by derivatizing actin with N-pyrenyliodoacetamide (Molecular Probes, Eugene Oreg.). Before use pyrene actin was diluted in depolymerization buffer (Buffer A: 0.5 mM ATP, 5 mM β-mercaptoethanol, 0.2 mM Tris, 0.2 mM $CaCl_2$, pH 7.4) to 20 µM, stored 1 h at 37° C. to reach monomer equilibrium and centrifuged at 250,000 g, 4° C. for 30 minutes, in an Optima™ TL Ultracentrifuge (Beckman) to pellet any remnant filamentous actin. The supernatant was withdrawn and stored in an ice water bath until used. Platelet poor plasma to be analyzed was diluted 1:5 in buffer B (0.1 M KCl, 0.2 mM $MgCl_2$, 0.2 mM $CaCl_2$, 0.5 mM ATP, 10 mM Tris, 0.5 mM mercaptoethanol, pH 7.4). Pyrene actin fluorescence was recorded using a luminescence fluorometer (FluoroMax-2®, JobinYvon-Spex Instruments S.A., Inc). Excitation and emission wavelengths were 366 and 386 nm, respectively. Pyrene actin was added to a final concentration of 1 µM in 280 µl buffer B containing 0.4 µM phalloidin, 1.5 mM $CaCl_2$ and 5 µl of diluted sample in 6×50 mm borosilicate glass culture tubes (Kimble). Nucleation was monitored over 240 s in the fluorometer following a fast vortex. The linear slope of the fluorescence increase was calculated between 100-200 s. All the samples were run in duplicates. Polymerization rate in each sample was converted to pGSN concentration by use of a standard curve of recombinant human pGSN.

Statistics: The level of pGSN in the blood and synovial fluid samples were expressed as mean±SD. Comparison between the matched blood and synovial fluid samples were analyzed by the paired t-test. Comparison of pGSN levels was also performed between the patient blood samples and the healthy controls. For further comparison patient material was stratified according to radiological findings (erosive RA vs. non-erosive RA). Differences in pGSN levels in the blood and synovial fluid between the groups were calculated separately employing the Mann-Whitney U test. For the evaluation of possible influence of the ongoing treatment on the pGSN levels, patient material was stratified according to DMARD treatment (treated vs. untreated). Comparison between the groups was performed using the Mann-Whitney U test. For all the statistical evaluation of the results, P-values below 0.05 were considered statistically significant.

Example 2

The Gelsolin Isoform Present in Synovial Fluid (SF) of RA Patients is the Plasma Isoform of Gelsolin (pGSN)

Figure 2:
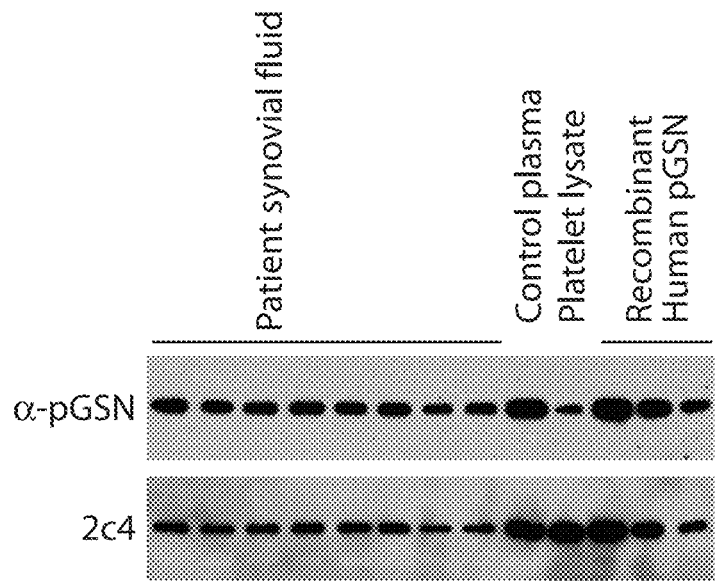
FIG. 2 is an immunoblot with an antibody specific for the plasma isoform of gelsolin showing that the gelsolin present in the synovial fluid (SF) of RA patients is composed mainly of the plasma isoform.
Figure 3:
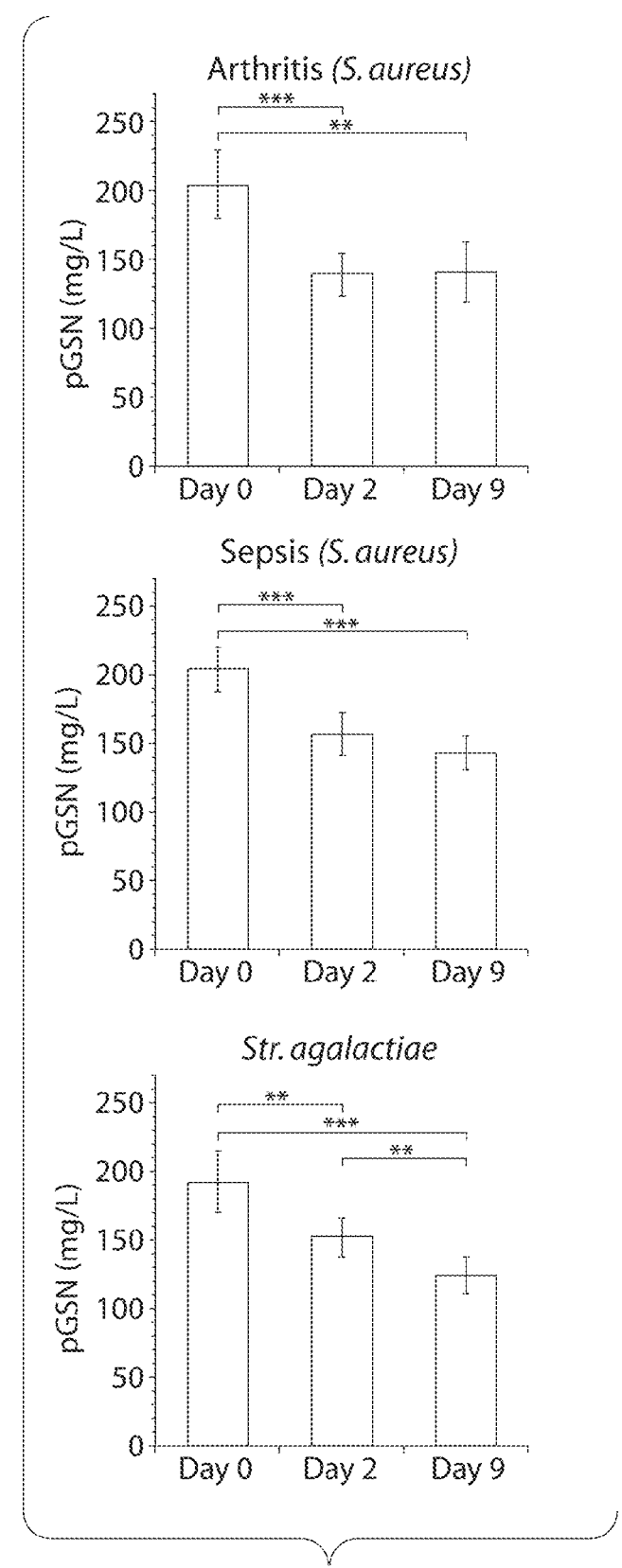
FIG. 3 is a set of histograms showing that plasma gelsolin (pGSN) concentrations are decreased in mouse models of septic arthritis: A) *Staphylococcus aureus* (*S. aureus*) induced arthritis, B) sepsis induced by *Staphylococcus aureus* (*S. aureus*) and C) *Streptococcus agalactiae* (*Str. agalactiae*) induced septic arthritis. The decrease occurred at the earliest time-point tested (two days post-inoculation).

Since gelsolin is produced as both an intracellular and extracellular isoform, each of which have the capacity to induce actin polymerization, we analyzed the origin of the gelsolin activity by immunoblotting with an antibody specific for the plasma isoform (α-pGSN). Gelsolin present in SF is composed mainly of the plasma isoform (FIG. 2). Plasma origin of gelsolin was also supported by a correlation between gelsolin levels in plasma and synovial fluid in the matched pair of samples (r=0.39, p=0.0006). However, pGSN activity in the SF samples from RA patients were significantly lower than that of plasma (pg/ml, 69±18 vs. 103±23, p=0.04) indicating local consumption.

Materials and Methods

Immunoblotting: The platelet poor plasmas or synovial fluids were diluted 1:100 in 1× sample buffer (SB, 20% glycerol, 4.6% Tris, 0.25 M Tris-HCl, 0.01% Bromphenol blue, 10% v/v 2-Mercaptoethanol, pH 6.8) for test of gelsolin isoform, vortexed briefly and boiled at 100° C. for 10 minutes. Samples (10 µl) were run on 10% SDS-PAGE (sodium dodecylsulfate polyacrylamide gelelectrophoresis) gels in a modified Laemmli system. Platelet lysate (2×10^8/ml, 5 µl) and human recombinant pGSN were run as negative and positive controls for pGSN respectively. Proteins were separated for 1.5 hour at 120V. Immobilon P membranes (PVDF, 0.45 µm; Millipore Corp., Bedford, Mass.) were soaked in methanol for 1 minute and transfer buffer (192 mM glycine, 25 mM Tris, 0.1% Sodium Dodecyl Sulfate, 20% Methanol) for 5 minutes, before transfer. The transfer was carried out at variable voltage, 1A for 90 minutes. The membranes were blocked overnight in PBS containing 0.05% Tween-20, 5% Carnation nonfat dry milk and 0.05% sodium azide pH 7.4 at 4° C. For pGSN a polyclonal antibody specific for the human plasma isoform was used (1:2000, 2 h, produced in the lab). For all isoforms of GSN a primary monoclonal 2c4 anti-gelsolin antibody was used (1:2500, 2 h, produced in the lab). Secondary antibodies used were rabbit-anti-mouse IgG (H+L)-HRP (1:5000, 80 min) and goat-anti-mouse IgG (H+L)-HRP conjugate respectively (1:3300, 80 min, Bio-Rad, Hercules, Calif.). Membranes were washed 3 times in PBS containing 0.05% Tween-20 between incubations.

Chemiluminescence detection was done using SuperSignal® West Pico Chemiluminescent Substrate for detection of HRP (PIERCE, Rockford, Ill.). The membranes were exposed to 2 ml each of SuperSignal® West Pico Stable Peroxide Solution and SuperSignal® West Pico Luminol/Enhancer Solution for 2 minutes. HyBlot CL autoradiography film (Denville Scientific, Inc., Metuchen, N.J.) was exposed to the membrane for 1 minute in a FBXC 810 autoradiography cassette (FiseherBiotech, Pittsburgh, Pa.). The film was developed using a M35A X-OMAT Processor (Kodak).

Example 3 pGSN is Decreased at Early Stages of an Experimental Mouse Model of Septic Arthritis/Sepsis Levels of circulating pGSN were decreased both during streptococcal and staphylococcal infection. This decrease occurred early during the time course of disease, beginning 2 days post-bacterial inoculation both in arthritic and septic groups of animals. Prior to injection (day 0), the average pGSN level of the mice was 200±20 mg/L. By day 2 pGSN levels decreased to 138±16 mg/L for the arthritic *Staphylococcus aureus* (*S. aureus*) treated ($7\times10^6$ cfu/mouse) animals, 157±15 mg/L for the septic *S. aureus* injected animals ($3.5\times10^7$ cfu/mouse), and 152±15 mg/L for the animals injected with *Streptococcus agalactiae* (*Str. agalactiae*) ($1\times10^7$ cfu/mouse). The pGSN levels at day 9 were 141±21, 151±15, and 124±13 mg/L, respectively. Only the animals injected with streptococcal bacteria displayed further decrease of the circulating pGSN levels at day 9. pGSN decrease was not related to the intensity of the infection since pGSN concentrations following administration of septic doses (5 times higher than the arthritic ones), which result in higher mortality, were not lower than those observed in the arthritic-dosed mice.

Materials and Methods

Induction of *S. aureus* arthritis and sepsis: Female 5-6 weeks old NMRI mice were purchased from ALAB (Stockholm, Sweden) and maintained in the animal facility of the Department of Rheumatology, University of Göteborg. They were housed 10-11 animals per cage under standard conditions of temperature and light and fed standard laboratory chow and water ad libitum. *S. aureus*, strain LS-1, originally isolated from a swollen joint of a spontaneously arthritic NZBxW mouse, strain Newman, as well as *Str. agalactiae* strain 6313, a clinical isolate belonging to serotype III, were used for the induction of septic arthritis and sepsis. Bacteria were kept frozen at −20° C., in PBS (0.13 M sodium chloride, 10 mM sodium phosphate, pH 7.4), containing 5% BSA and 10% dimethyl sulfoxide, until used. Before the injection, the bacterial solution was thawed, washed twice with PBS, and adjusted with PBS to the desired concentration. Mice were injected into the tail vein with a suspension of *S. aureus* or *Str. agalactiae* in 0.2 ml PBS. Viable counts in the leftover solution were determined to check the exact number of bacteria injected and presented as colony forming units (cfu/ml).

All the mice were monitored individually during the observation period of 8-9 days by assessment of joint appearance, weight, general appearance, alertness, and skin abnormalities. Blood samples were obtained from the tail vein in a sterile tube without anticoagulant and remained to clot for 6-8 hours. The samples were centrifuged at 3000×g for 15 min, serum was aliquoted and kept frozen at 70° C. until used.

Experimental protocol: twenty mice obtained intravenously (i.v.) a septic (LS-1, $4\times10^7$ cfu/mouse, n=10) or arthritogenic ($7\times10^6$ cfu/mouse, n=10) dose of *S. aureus*. Additional 10 mice obtained intravenously a septic dose of *Str. agalactiae* ($1\times10^7$ au/mouse). On days −3, 2, 4, 6, and 9 blood samples were collected by the tail vein incision for the determination pGSN levels. On day 9 all mice were sacrificed by cervical dislocation. pGSN level was determined with the same method as for the human samples (pyrene actin nucleation assay).

Example 4 pGSN Supplementation to Mice Delays Development of Arthritis

Supplementation of mice with recombinant gelsolin was performed over 7 days with 24 h interval starting immediately before bacterial inoculation ($4\times10^7$/ml). Five mice received gelsolin while 7 mice received PBS and were used as controls. During the first 9 days of staphylococcal infection no difference was observed in gelsolin-treated and the control groups with respect to weight loss, survival rate or development of arthritis. However, fewer of the gelsolin-treated mice developed arthritis on day 3 (1 treated vs 4 non-treated—See Table 1).

TABLE 1

Dynamics of weight, survival and development of arthritis in NMRI mice infected intravenously with *S. aureus*.

|  | Day 1 | Day 3 | Day 5 | Day 7 | Day 9 | Day 28 |  |
|---|---|---|---|---|---|---|---|
| Gelsolin | 31.5 g | 30.0 g | 27.2 g | 25.3 g | 25.7 g | 30.8 g | Mean weight |
| PBS controls | 31.2 | 28.5 | 27.7 | 22.9 | 25.4 | 32.4 | Mean weight |
|  | 5G/7C | 5G/7C | 5G/7C | 5G/7C | 3G/6C | 2G/6C | Survival |
|  | 1G/0C | 1G/4C | 2G/4C | 3G/4C | 2G/1C | 2G/2C | Arthritis |

G = plasma gelsolin,
C = Control.

Materials and Methods

Twelve mice were injected intravenously (i.v.) with a septic dose of *S. aureus* (Newman, $4\times10^7$ cfu/mouse). Five mice received recombinant human pGSN intra-peritoneally (i.p.) during days 0-7 and the remaining 7 mice received PBS. The mice were monitored individually up to day 28 and signs of arthritis, weight, general appearance, and alertness were followed.

Recombinant pGSN was produced in *E. coli*, refolded with GSSG, formulated in 0.1 M NaCl and 1 mM CaCl$_2$ by Biogen-Idec, Inc. (Cambridge, Mass.) and kept at −70° C. prior to use. Mice were injected with recombinant pGSN i.p. (6 mg/mouse) one hour prior to the bacterial challenge and continued with 24-hours interval (3 mg/mouse) during 7 days. The controls received a corresponding volume of PBS.

Example 5

The hypothesis that administration of gelsolin could impact upon the inflammatory processes is tested in a rodent model of collagen induced arthritis (CIA), an autoimmune model that resembles rheumatoid arthritis. CIA is inducible in inbred DBA/1 male mice by priming intradermally with heterologous or homologous collagen II (about 50 microgram) in Freunds complete adjuvant and 2 weeks later boosting with the same amount of collagen II in Freunds incomplete adjuvant. The arthritis develops approximately 3 weeks after the priming dose and reaches its maximum within 8 weeks post priming. The mice have high levels of collagen II specific antibodies, collagen II specific T cells as well as signs of systemic inflammation (e.g. production of IL-6, TNF etc). Locally in the joints one observes both overwhelming inflammatory infiltrates (consisting of T cells, macrophages, neutrophils and fibroblasts) as well as severe destruction of cartilage and subchondral bone. These features mimic well the process seen in human rheumatoid arthritis (Myers et al., Life Sciences 61, p 1861-1878, 1997).

In a therapeutic test one set of test animals receives, for example, subcutaneously 8 mg of bovine serum albumin or 8 mg human recombinant plasma gelsolin once on day ten from the start of therapy (1×) or three doses on days 2, 5 and 10 (3×). This route of administration and dosing has previously been shown to raise gelsolin levels depleted 50% by sepsis to normal. Several parameters of the disease (e.g., clinical signs and symptoms, onset, progression, severity, and remission of symptoms) are measured.

In summary, our findings support the two aspects of the hypothesis posed, namely, that reductions in plasma gelsolin levels precede manifestations of inflammatory diseases such as rheumatoid arthritis and that systemic treatment with plasma gelsolin prevents and/or suppresses these manifestations. One clinical correlate of these observations is that serial monitoring of plasma gelsolin levels could become part of the management strategy of inflammatory diseases such as rheumatoid arthritis, flagging when to intensify therapy. Another correlate is that prophylactic elevation of plasma gelsolin levels might protect patients from the sequelae of inflammation.

Although not intending to be bound by any particular mechanism or theory, it is presumed that plasma gelsolin is depleted from the blood during inflammatory diseases (such as rheumatoid arthritis (RA)) and is localized or sequestered at the site of injury/inflammation (the joint space in rheumatoid arthritis). It is believed that plasma gelsolin functions at the site of inflammation by binding to inflammatory mediators and prevents them from causing further damage by inhibiting their actions on cellular receptors. This is supported by the fact that plasma gelsolin in vitro binds to some inflammatory mediators such as lysophosphatidic acid (LPA), Aβ (Alzheimer) peptide, diadenosine 5',5'''-P1,P3-triphosphate (Ap3A), fibronectin, fibrinogen and lipopolysaccharide (LPS) and decreases certain cellular responses to platelet activating factor (PAF). Additionally, damaged cells at the inflamed joint release actin and gelsolin binds to actin. Gelsolin may have a protective role by severing filamentous actin that might otherwise be, toxic. We believe that gelsolin has an anti-inflammatory effect, but when the inflammation is severe and prolonged as in RA, gelsolin supplementation might be beneficial in reducing or treating the inflammation. Sequestration or recruitment of gelsolin to the site of inflammation (such as the joint space in rheumatoid arthritis) could explain why the plasma levels are reduced although other explanations are also possible.

EQUIVALENTS

The foregoing written specification is considered to be sufficient to enable one ordinarily skilled in the art to practice the invention. The present invention is not to be limited in scope by the example(s) provided, since the example(s) are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

We claim:

1. A method for treating a subject having an inflammatory disease comprising:
   administering to a subject in need of such a treatment an effective amount of plasma gelsolin to treat the subject, wherein the inflammatory disease is rheumatoid arthritis or inflammatory bowel disease.

2. The method of claim 1, wherein the subject is otherwise free of indications calling for treatment with gelsolin.

3. The method of claim 1, wherein the inflammatory disease is rheumatoid arthritis.

4. The method of claim 1, wherein the inflammatory disease is inflammatory bowel disease.

5. A method for treating a subject having an inflammatory disease comprising:
   administering to a subject in need of such a treatment an effective amount of plasma gelsolin to raise the level of gelsolin in the subject above a predetermined value, wherein the inflammatory disease is rheumatoid arthritis or inflammatory bowel disease.

6. The method of claim 5, wherein the subject is otherwise free of indications calling for treatment with gelsolin.

7. The method of claim 5, wherein the predetermined level of gelsolin is a level of gelsolin in an apparently healthy control population.

8. The method of claim 5, wherein the predetermined value of gelsolin is about 250 mg/L of plasma or higher.

9. The method of claim 5, wherein the inflammatory disease is rheumatoid arthritis.

10. The method of claim 5, wherein the inflammatory disease is inflammatory bowel disease.

11. A method for treating a subject to reduce the risk of an inflammatory disease comprising:
   (i) selecting a subject who has a below-normal level of gelsolin and
   (ii) administering to the subject plasma gelsolin and/or a second agent in an effective amount to reduce the risk of the subject developing the inflammatory disease, wherein the inflammatory disease is rheumatoid arthritis or inflammatory bowel disease.

12. The method of claim 11, wherein the subject is otherwise free of indications calling for treatment with gelsolin.

13. The method of claim 11, wherein the inflammatory disease is rheumatoid arthritis.

14. The method of claim 11, wherein the inflammatory disease is inflammatory bowel disease.

15. A method for treating a subject to reduce the risk of an inflammatory disease comprising:
   (i) selecting a subject who has a below-normal level of gelsolin and
   (ii) administering to the subject plasma gelsolin and/or a second agent in an effective amount to raise the level of gelsolin in the subject above a predetermined value, wherein the inflammatory disease is rheumatoid arthritis or inflammatory bowel disease.

16. The method of claim 15, wherein the subject is otherwise free of indications calling for treatment with gelsolin and/or is apparently healthy.

17. The method of claim 15, wherein the inflammatory disease is rheumatoid arthritis.

18. The method of claim 15, wherein the inflammatory disease is inflammatory bowel disease.

* * * * *